US012601678B2

(12) United States Patent
Choa et al.

(10) Patent No.: US 12,601,678 B2
(45) Date of Patent: Apr. 14, 2026

(54) COMPLEX GAS SENSOR, METHOD FOR MANUFACTURING SAME, AND METHOD FOR CONTROLLING COMPLEX GAS SENSOR

(71) Applicant: INDUSTRY-UNIVERSITY COOPERATION FOUNDATION HANYANG UNIVERSITY ERICA CAMPUS, Ansan-si (KR)

(72) Inventors: Yong-Ho Choa, Seongnam-si (KR); Han Kim, Seoul (KR); Byungkwon Jang, Pyeongtaek-si (KR); Ji Young Park, Ansan-si (KR); Min Seob Lim, Seoul (KR)

(73) Assignee: INDUSTRY-UNIVERSITY COOPERATION FOUNDATION HANYANG UNIVERSITY ERICA, Ansan-si (KR)

( * ) Notice: Subject to any disclaimer, the term of this patent is extended or adjusted under 35 U.S.C. 154(b) by 281 days.

(21) Appl. No.: 18/266,504

(22) PCT Filed: May 31, 2022

(86) PCT No.: PCT/KR2022/007733
§ 371 (c)(1),
(2) Date: Jun. 9, 2023

(87) PCT Pub. No.: WO2023/153561
PCT Pub. Date: Aug. 17, 2023

(65) Prior Publication Data
US 2024/0361235 A1      Oct. 31, 2024

(30) Foreign Application Priority Data

Feb. 9, 2022    (KR) ........................ 10-2022-0016626
Apr. 28, 2022   (KR) ........................ 10-2022-0052559
Apr. 28, 2022   (KR) ........................ 10-2022-0052560

(51) Int. Cl.
*G01N 21/33*      (2006.01)
*G01N 33/00*      (2006.01)

(52) U.S. Cl.
CPC ......... *G01N 21/33* (2013.01); *G01N 33/0027* (2013.01)

(58) Field of Classification Search
None
See application file for complete search history.

(56) References Cited

U.S. PATENT DOCUMENTS

| | | | |
|---|---|---|---|
| 11,029,271 B2 | 6/2021 | Lee et al. | |
| 11,353,434 B2 * | 6/2022 | Oki ................... | G01N 33/0018 |
| 2021/0190721 A1 | 6/2021 | Drmosh et al. | |

FOREIGN PATENT DOCUMENTS

| | | | |
|---|---|---|---|
| JP | 08-010202 B | * | 2/1988 |
| JP | 5-240822 A | | 9/1993 |

(Continued)

OTHER PUBLICATIONS

Zamani et al. "Capacitive-type gas sensors combining silicon semi-conductor and NaNO2-based solid electrolyte for NO2 detection." *Sensors and Actuators B: Chemical* vol. 109. Issue 2, 2005 (pp. 299-306).

*Primary Examiner* — Edwin C Gunberg
(74) *Attorney, Agent, or Firm* — NSIP Law

(57) ABSTRACT

The present disclosure relates to a gas sensor using photo-active energy and capacitance, and provides a complex gas sensor including a light source configured to irradiate light, and a gas detection part in which adsorption of a target gas is promoted by the light and whose capacitance changes according to the adsorption of the target gas.

19 Claims, 28 Drawing Sheets

10

(56)     References Cited

FOREIGN PATENT DOCUMENTS

| | | | |
|---|---|---|---|
| JP | H05240822 A * | 9/1993 | |
| JP | 8-10202 B2 | 1/1996 | |
| KR | 10-1999-0062777 A | 7/1999 | |
| KR | 10-2007-0104810 A | 10/2007 | |
| KR | 10-0775412 B1 | 11/2007 | |
| KR | 10-0866589 B1 | 11/2008 | |
| KR | 10-1201896 B1 | 11/2012 | |
| KR | 10-1659320 B1 | 9/2016 | |
| KR | 10-2017-0030871 A | 3/2017 | |
| KR | 10-1736795 B1 | 5/2017 | |
| KR | 10-1750010 B1 | 6/2017 | |
| KR | 10-2020-0066461 A | 6/2020 | |
| KR | 10-2172896 B1 | 11/2020 | |
| WO | WO-2021028157 A1 * | 2/2021 | ........... H10F 77/122 |

* cited by examiner

【FIG.1】
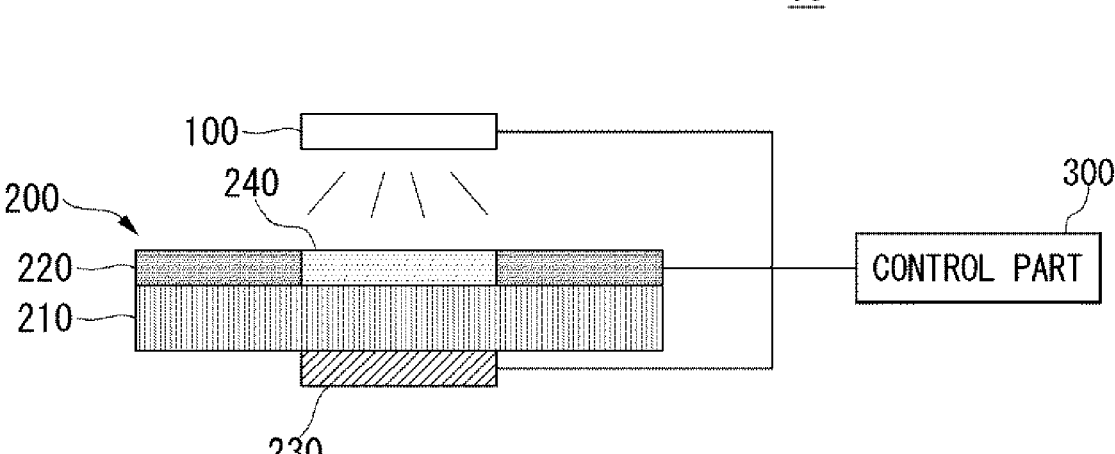

【FIG.2】
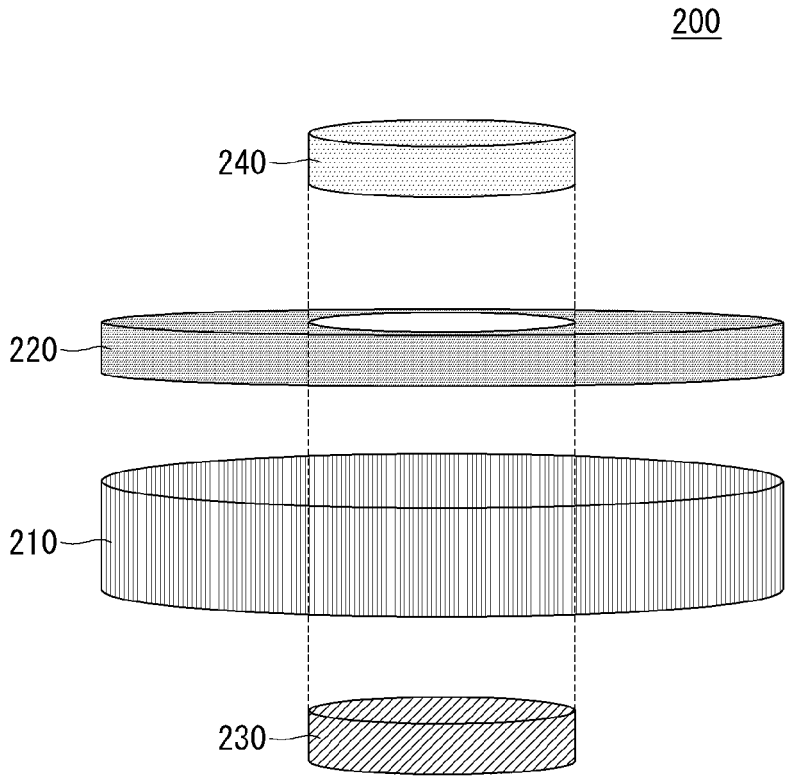

【FIG.3A】
220
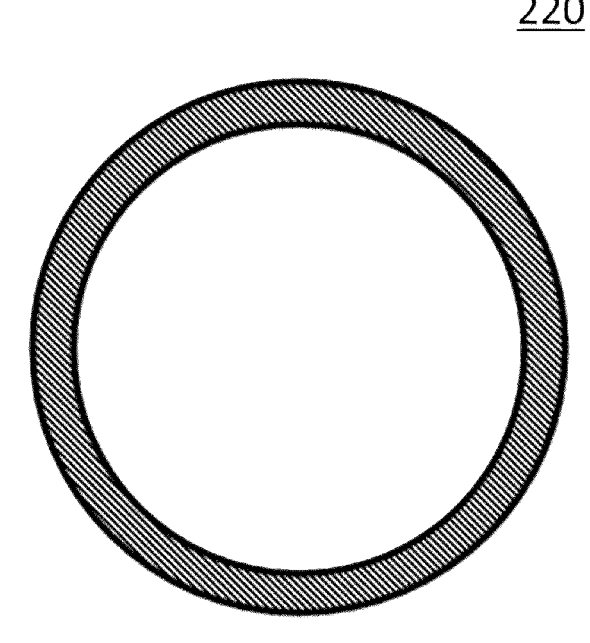
【FIG.3B】
230
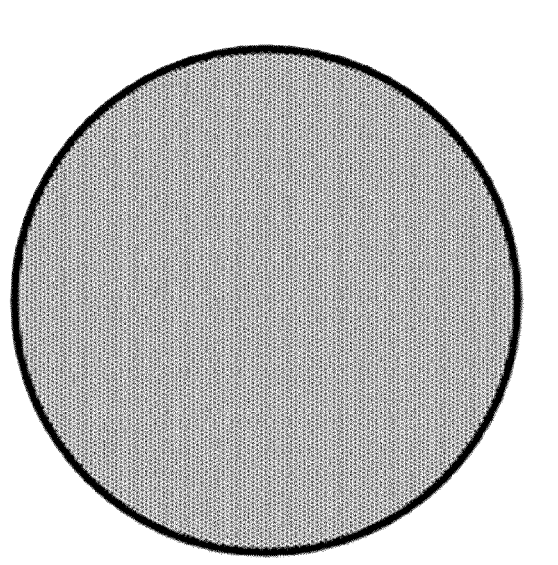

【FIG.4】
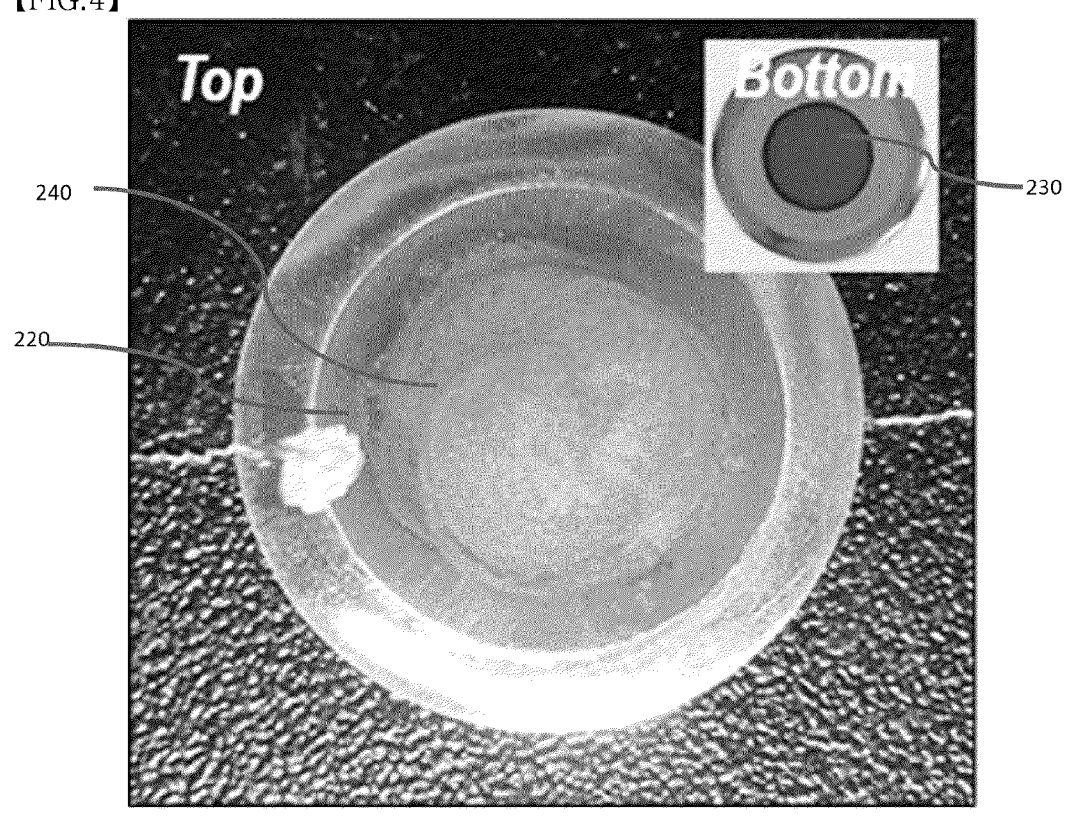

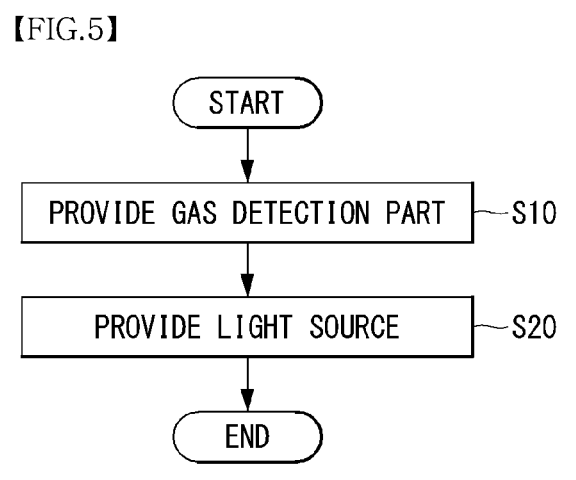

【FIG.5】

【FIG.6】
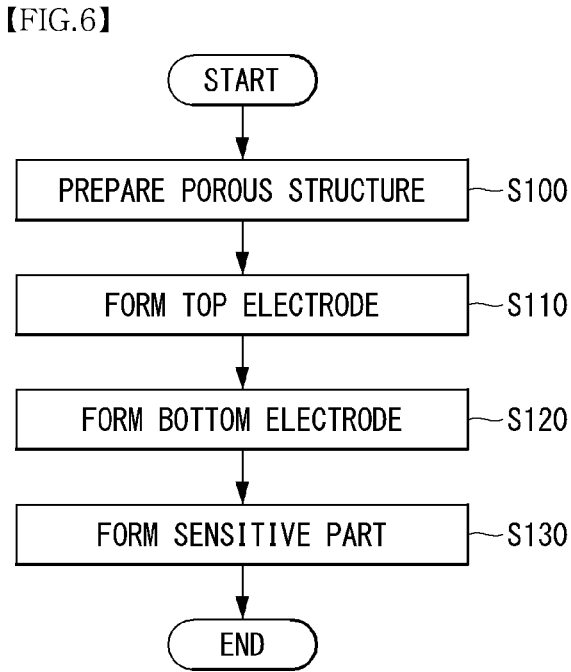

【FIG.7A】
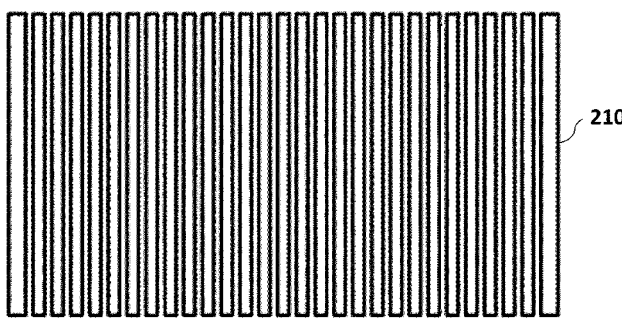
210
【FIG.7B】
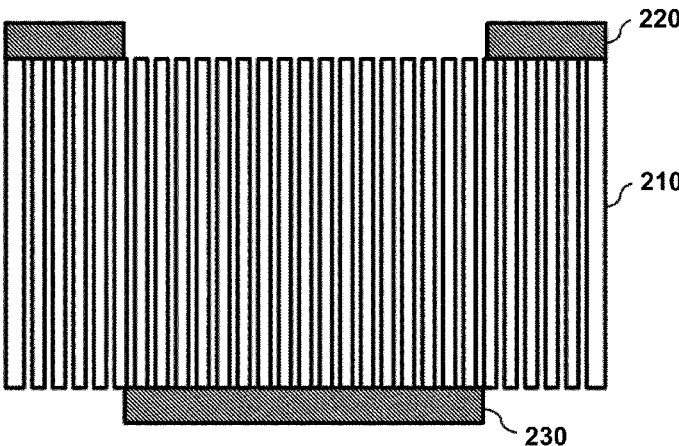
220
210
230
【FIG.7C】
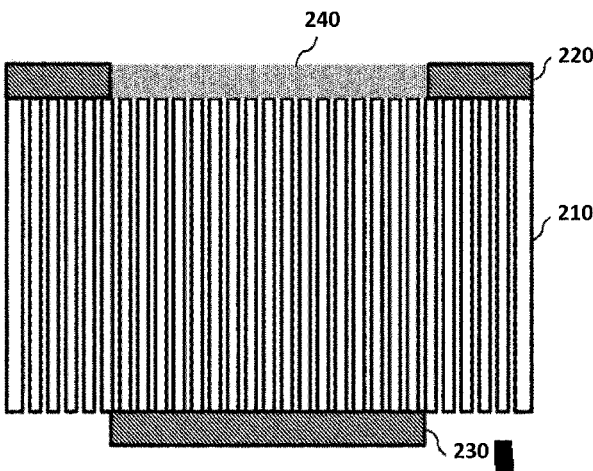
240
220
210
230

【FIG.8】
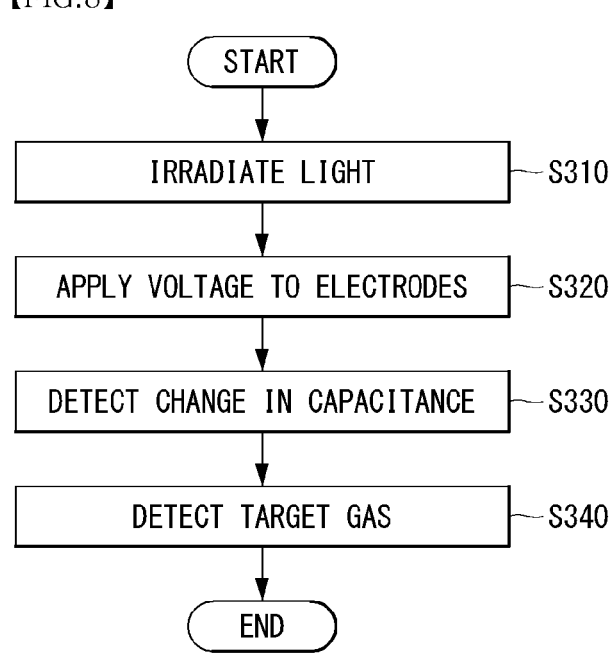
【FIG.9】
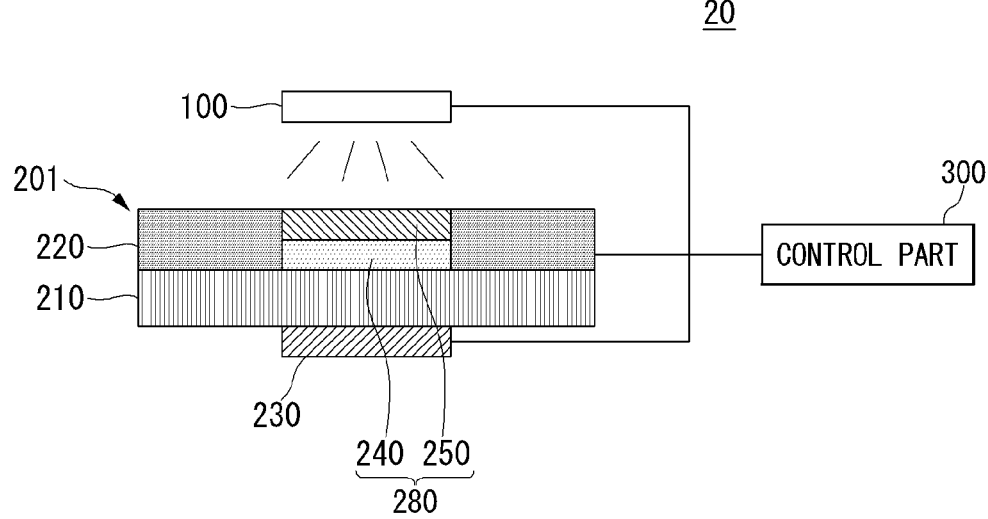

【FIG.10】
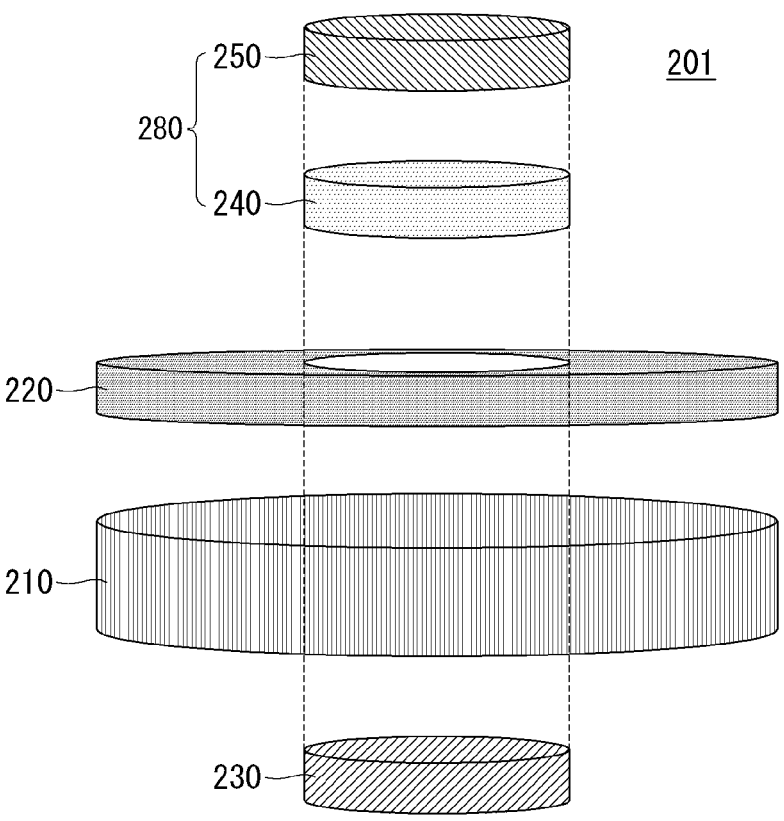
【FIG.11】
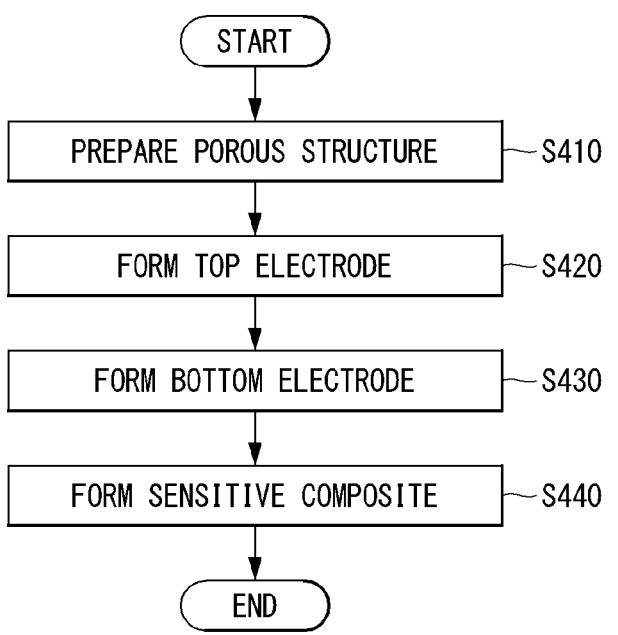

【FIG.12】
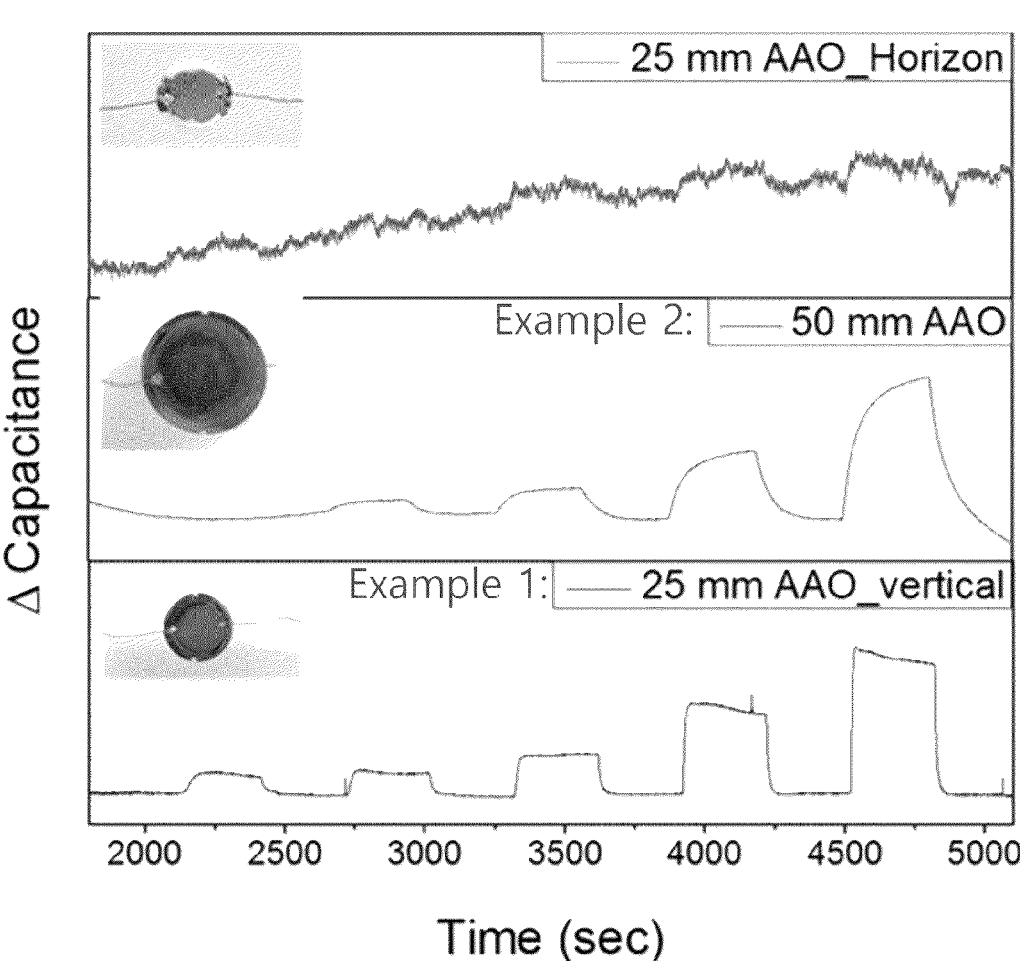
Time (sec)

【FIG.13】
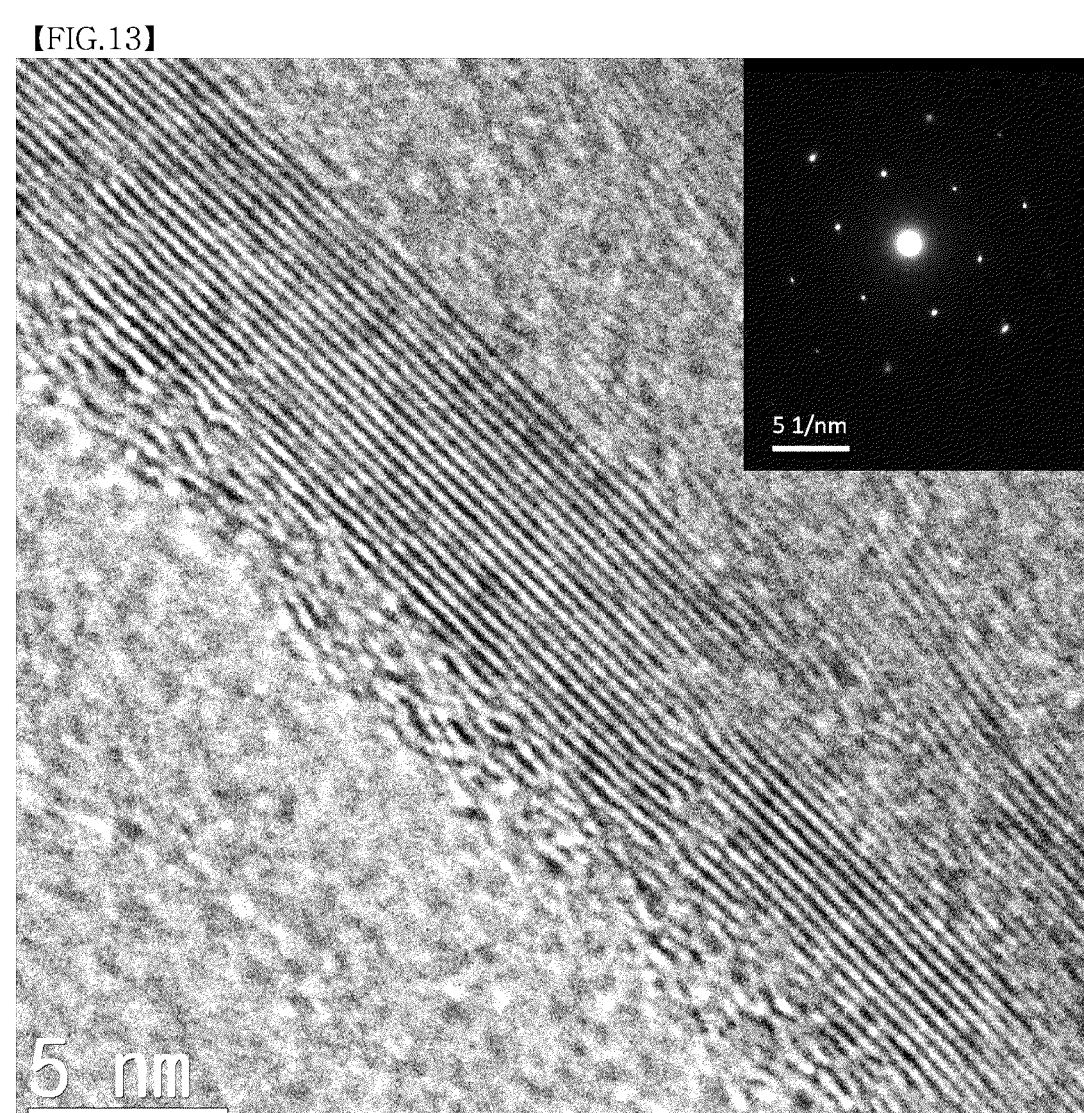

【FIG.14A】
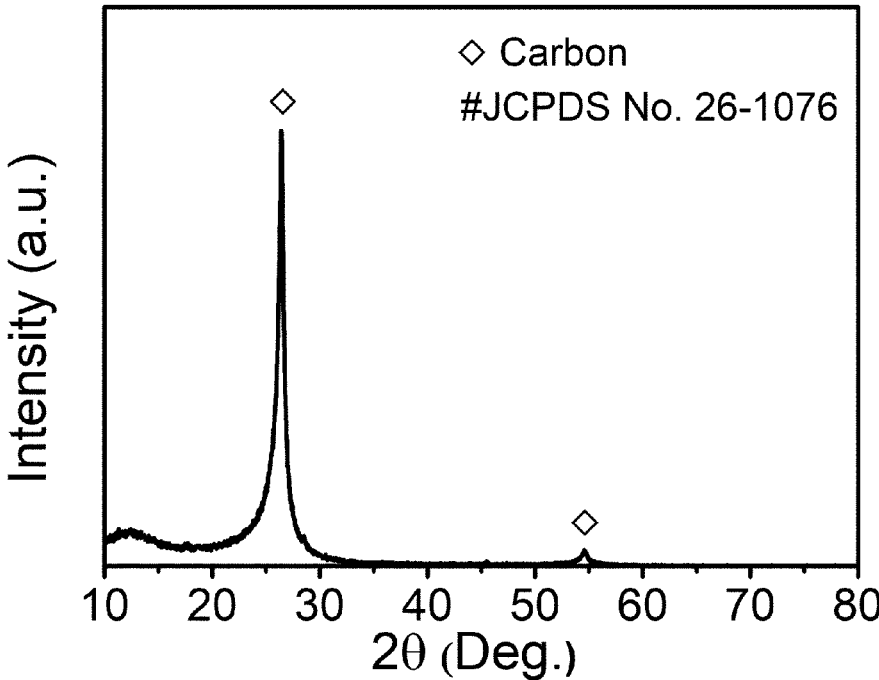
【FIG.14B】
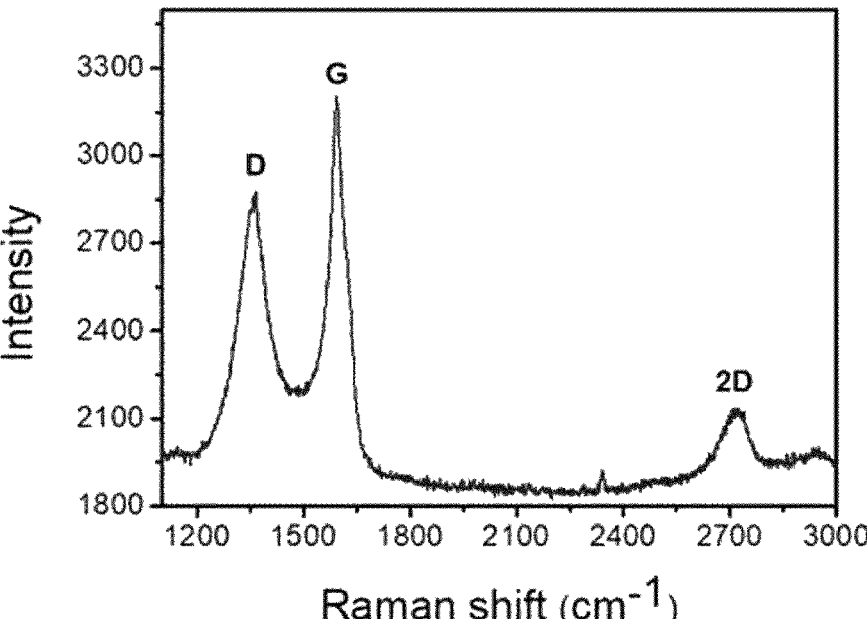

【FIG.15】
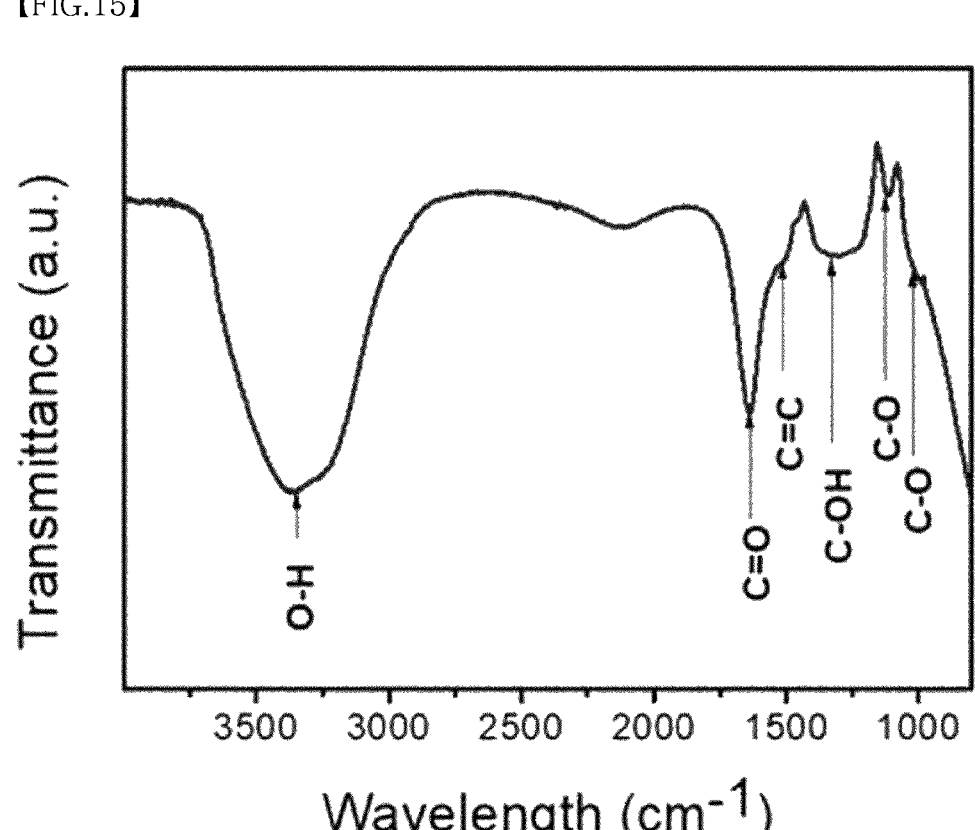

【FIG.16】
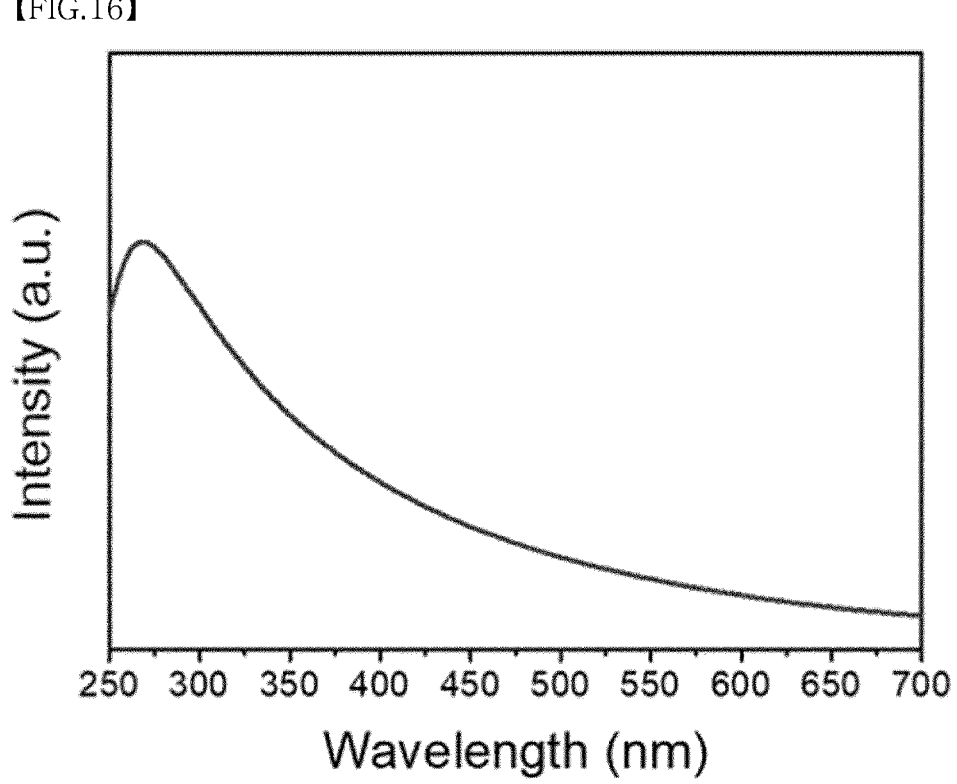

【FIG.17A】
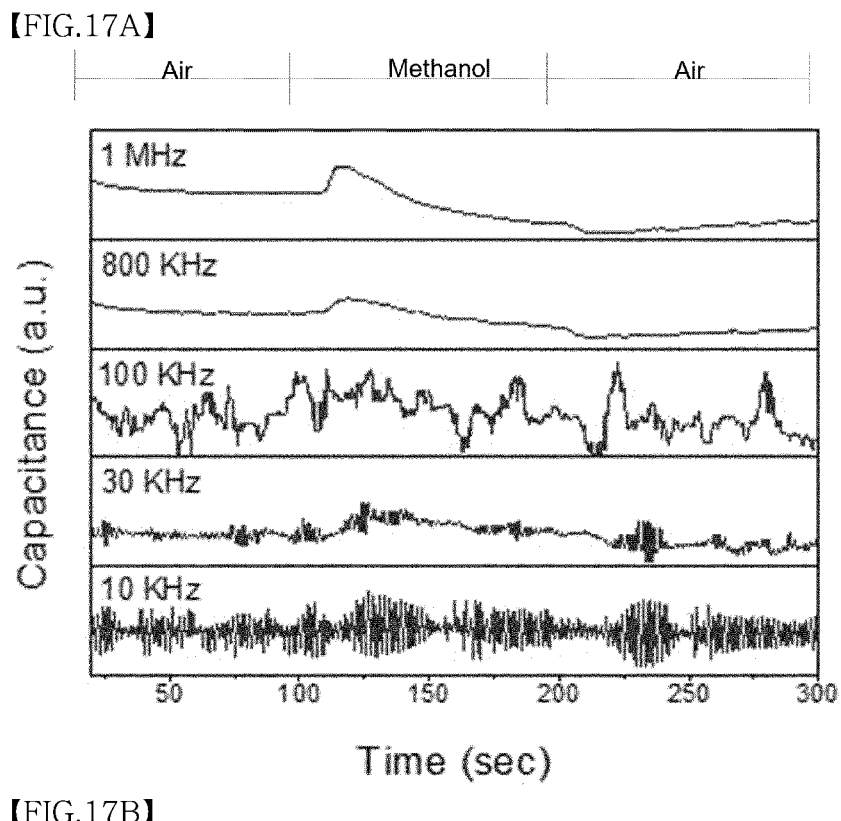
【FIG.17B】
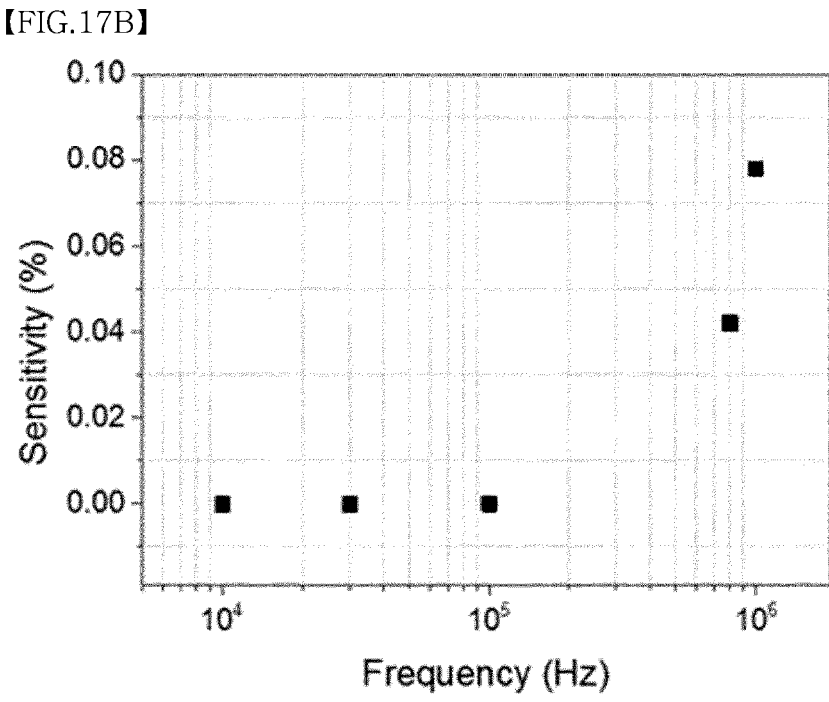

【FIG.18A】
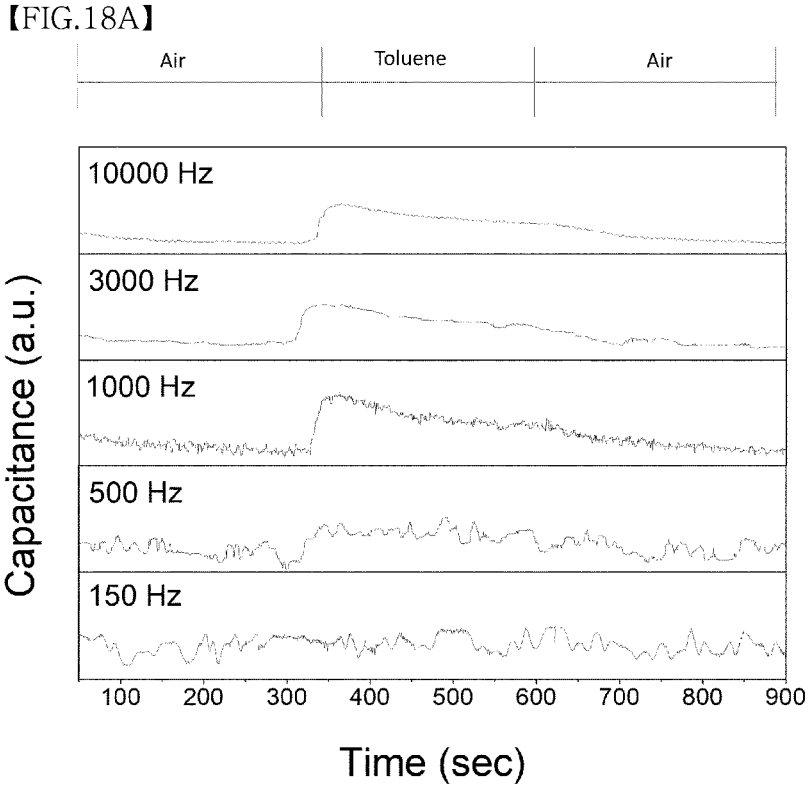
【FIG.18B】

【FIG.19A】
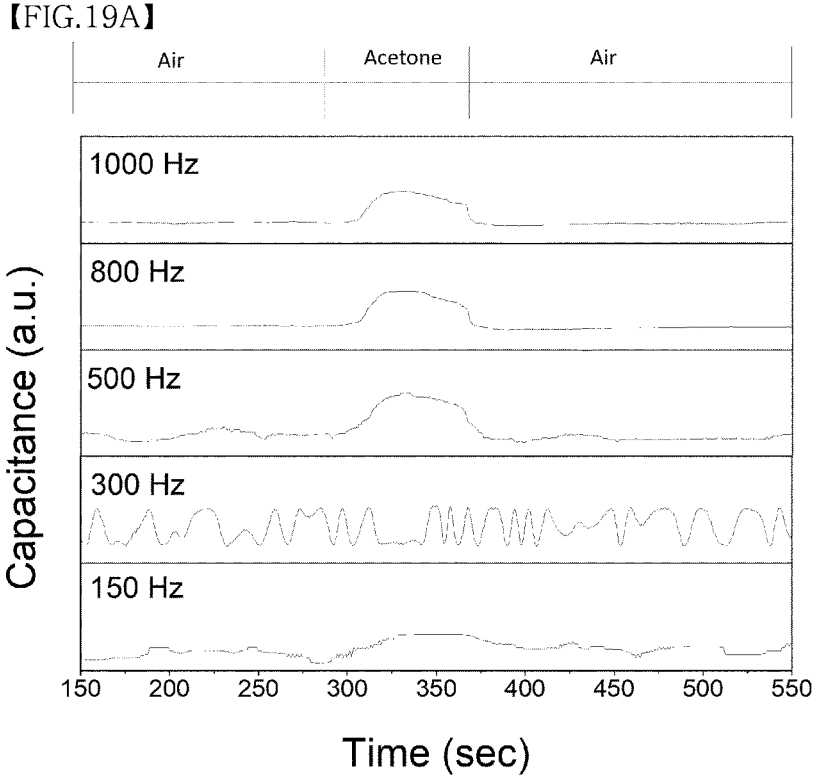
【FIG.19B】
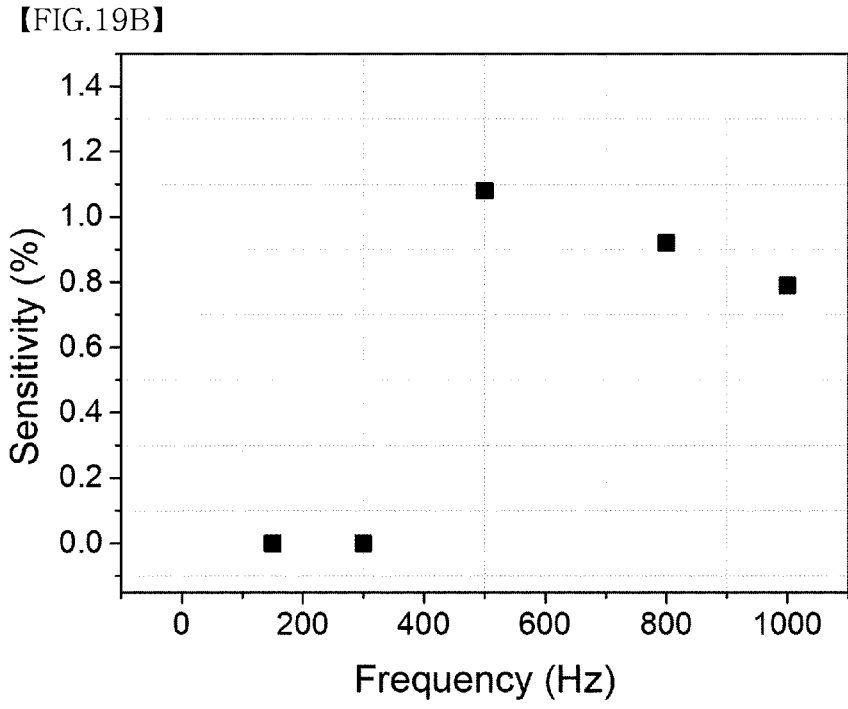

【FIG.20】
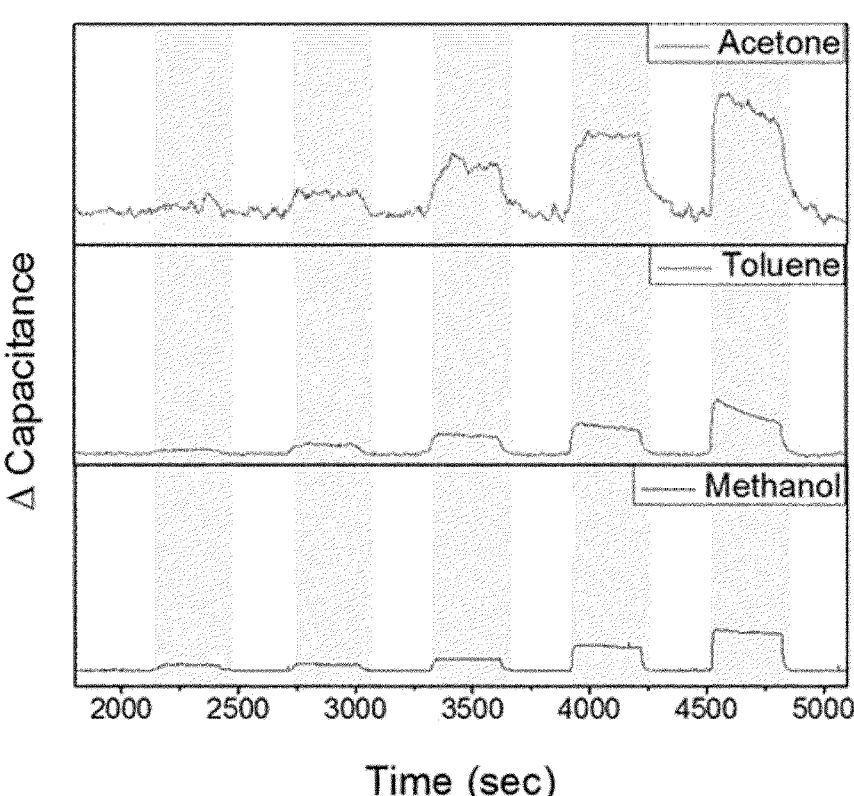
Time (sec)
【FIG.21】
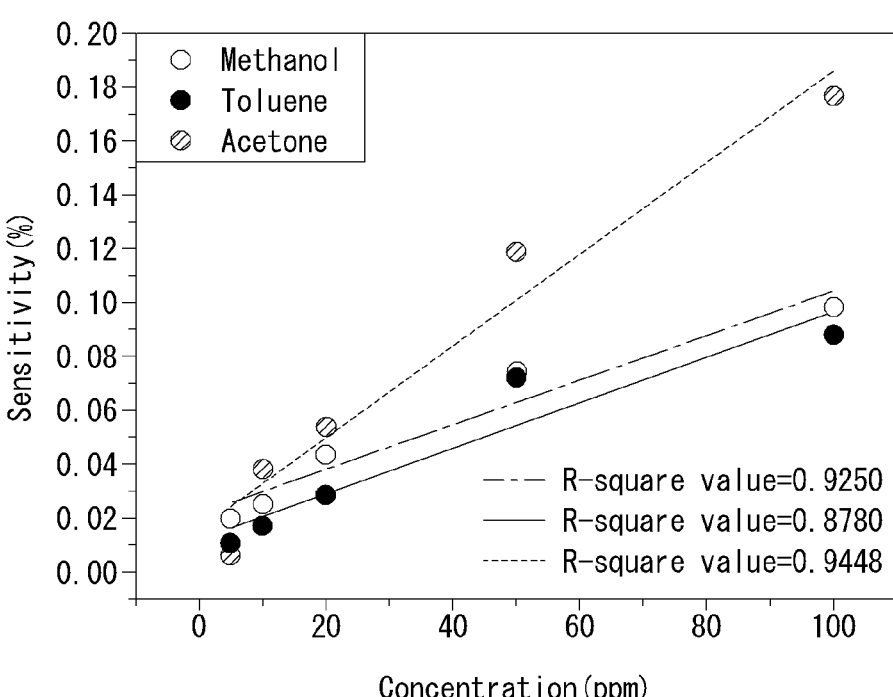
Concentration(ppm)

【FIG.22】
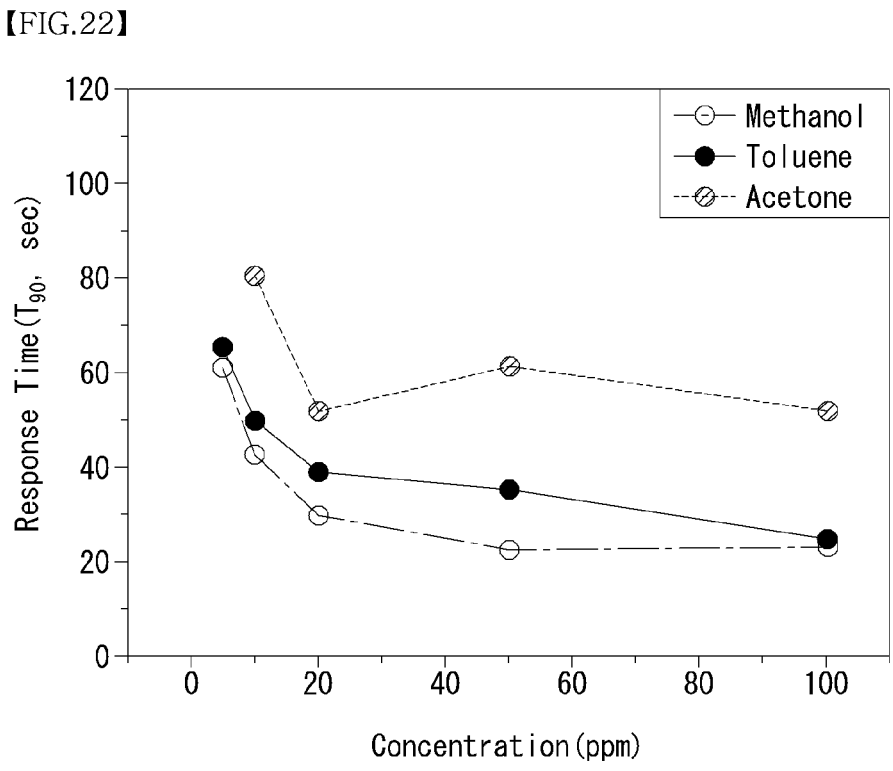
【FIG.23】
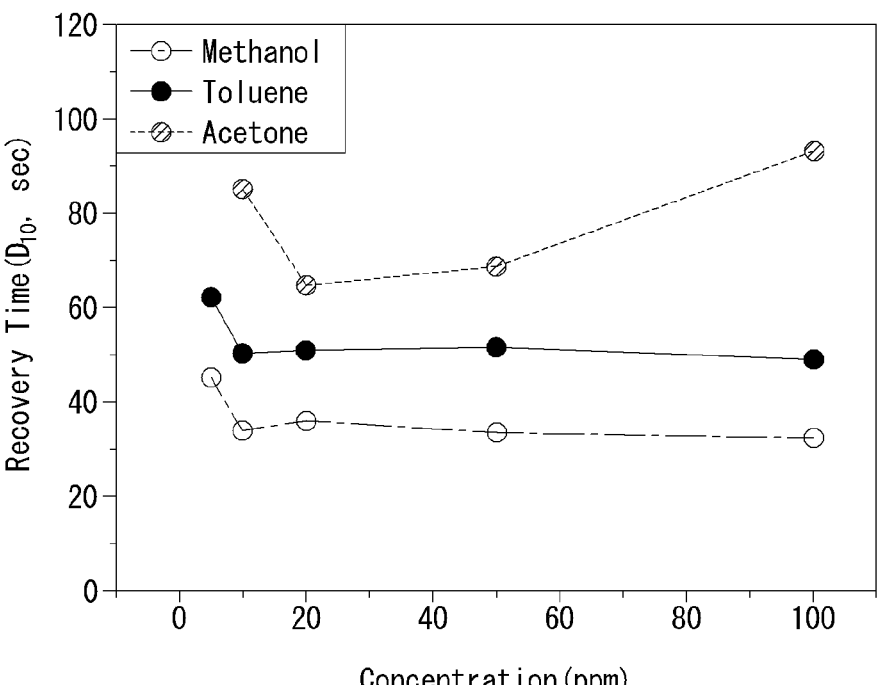

【FIG.24A】
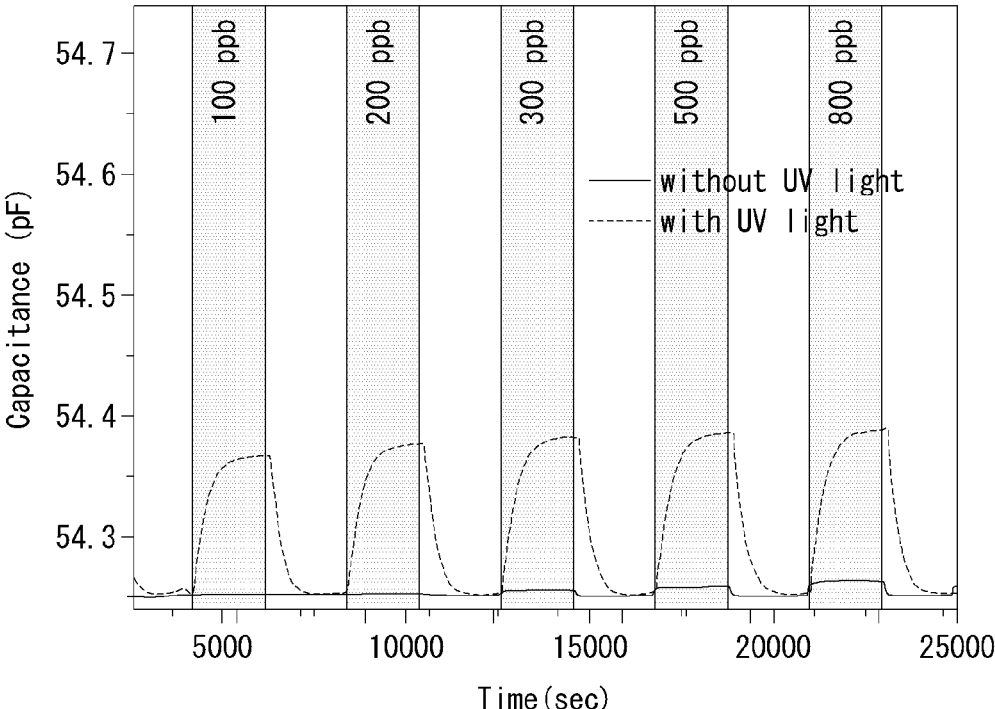
【FIG.24B】
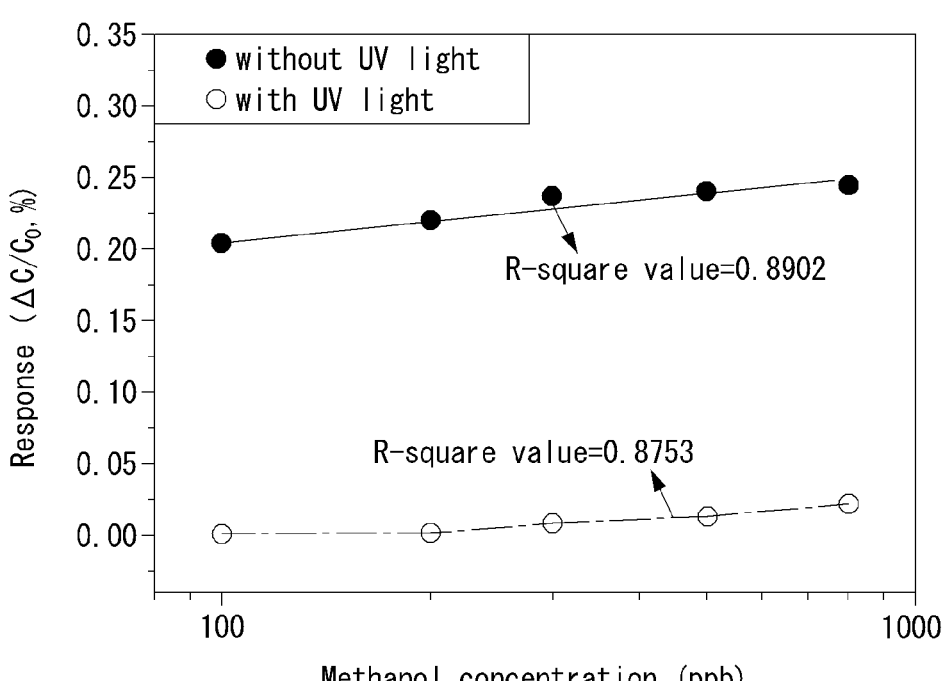

【FIG.25A】
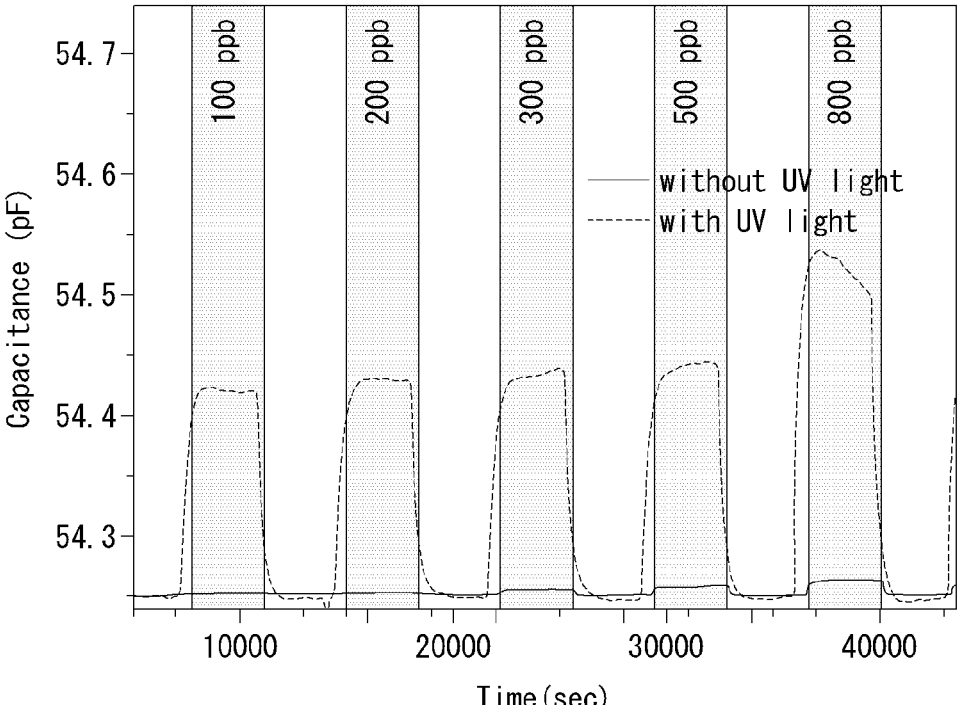
【FIG.25B】
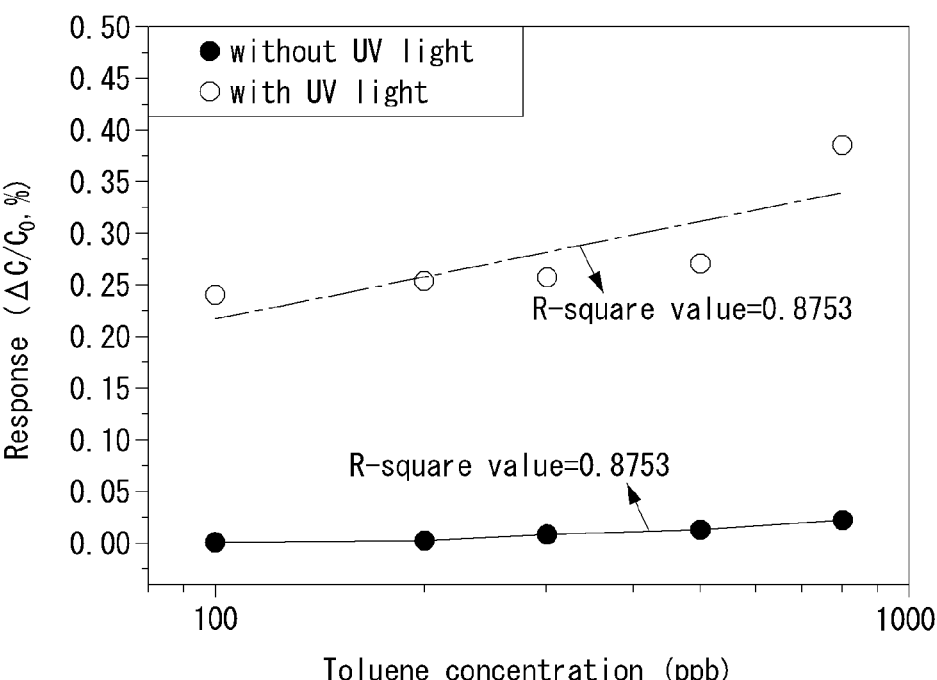

【FIG.26A】
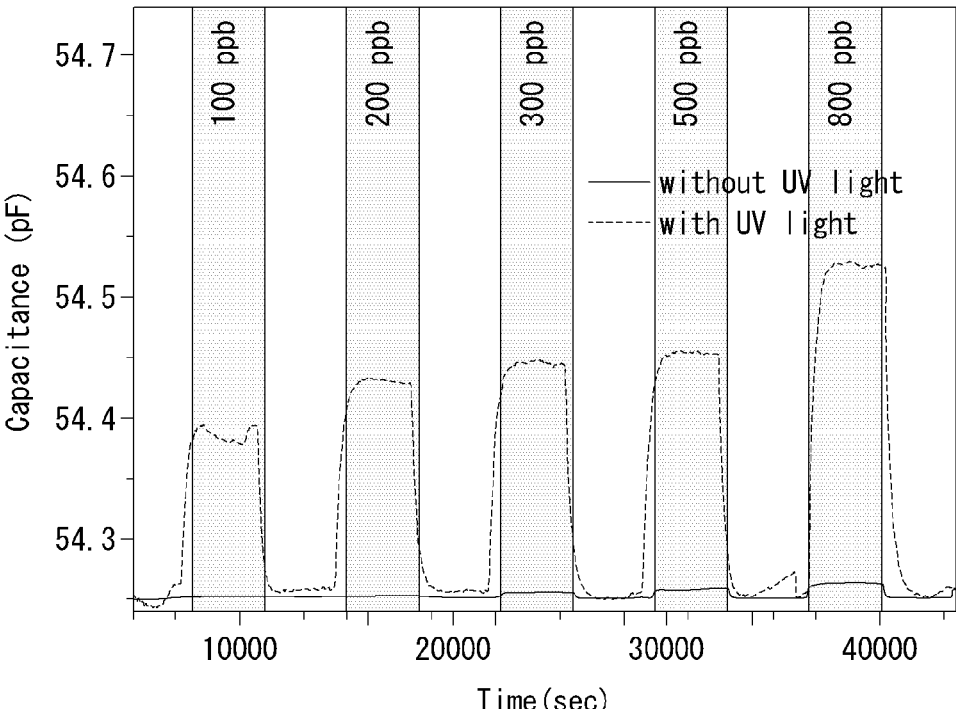
【FIG.26B】
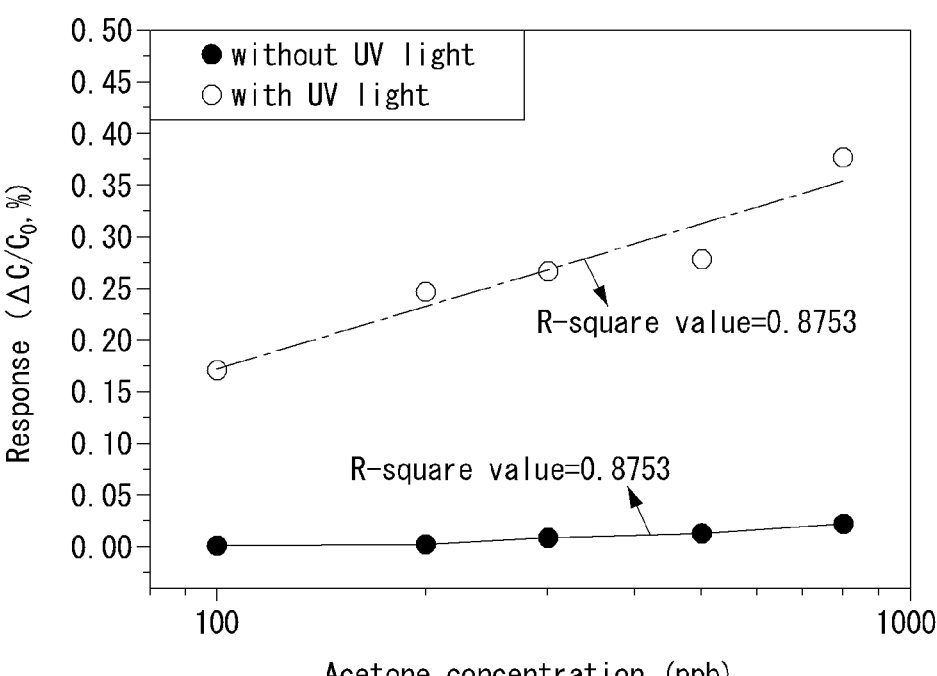

【FIG.27】
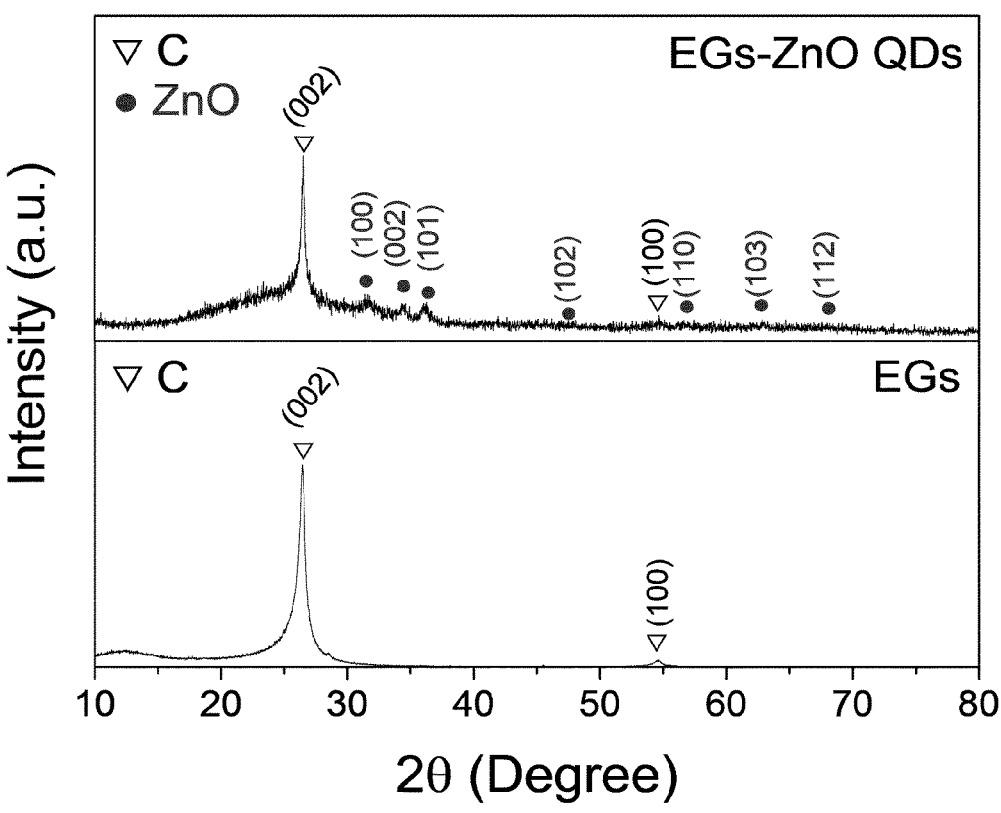
【FIG.28】
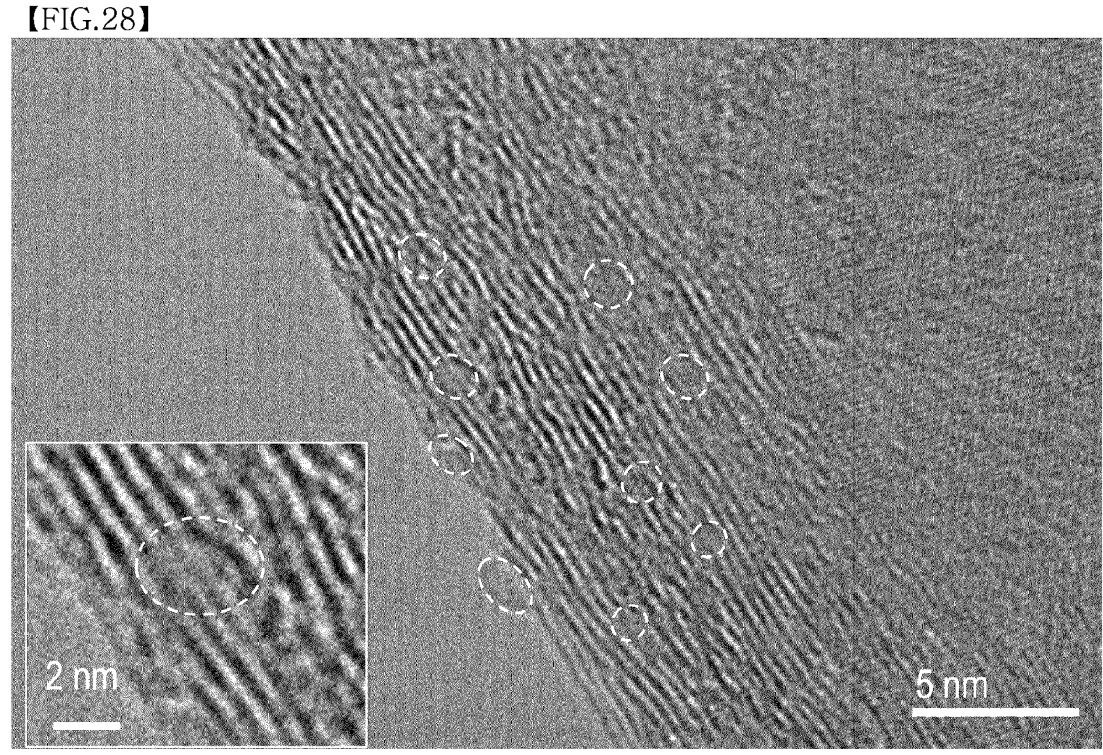

【FIG.29A】
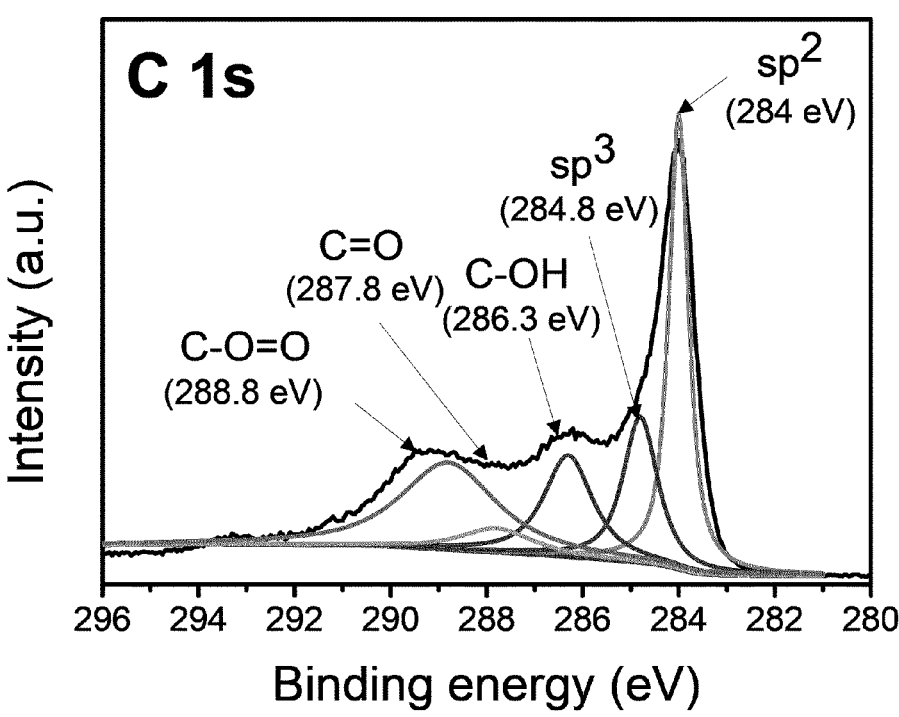
【FIG.29B】
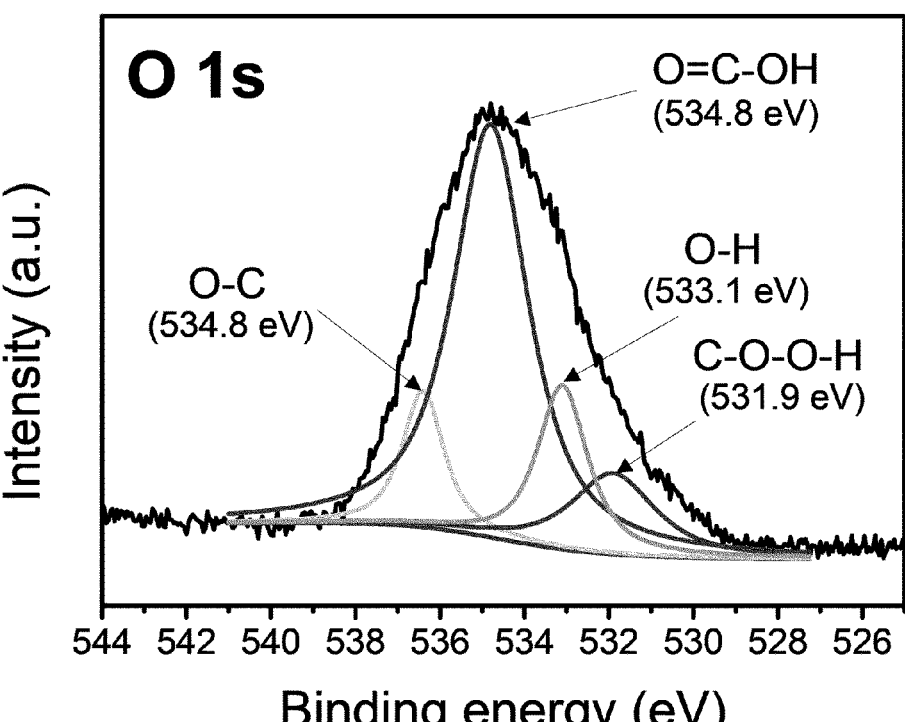

【FIG.30A】
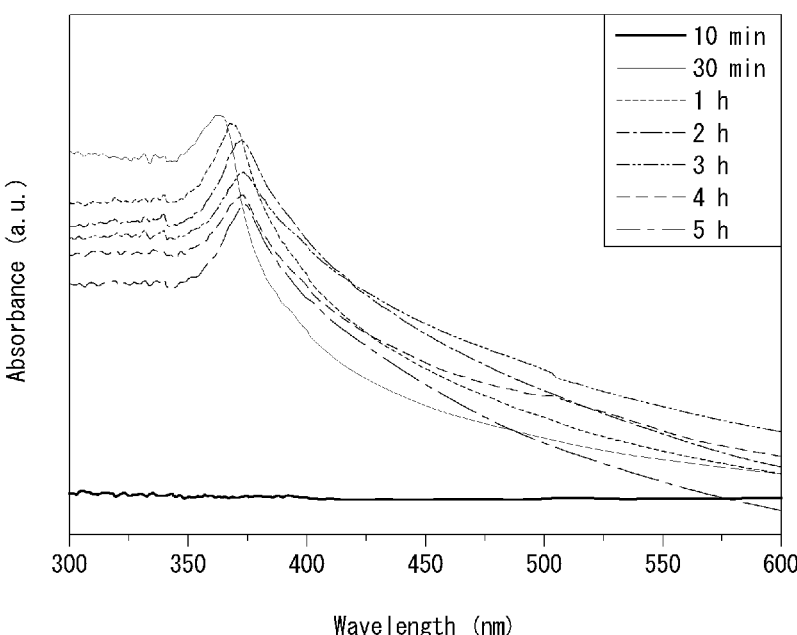
【FIG.30B】
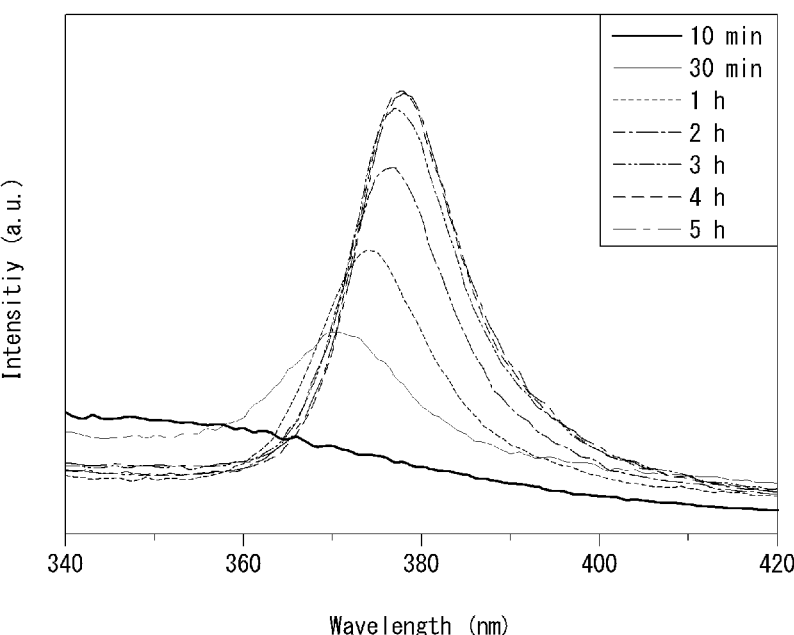

【FIG.31A】
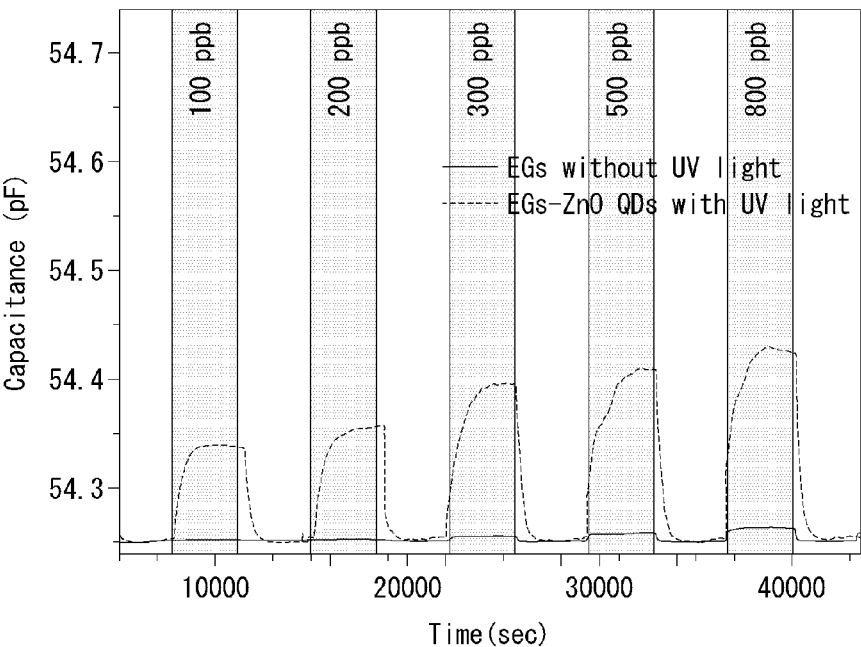
【FIG.31B】
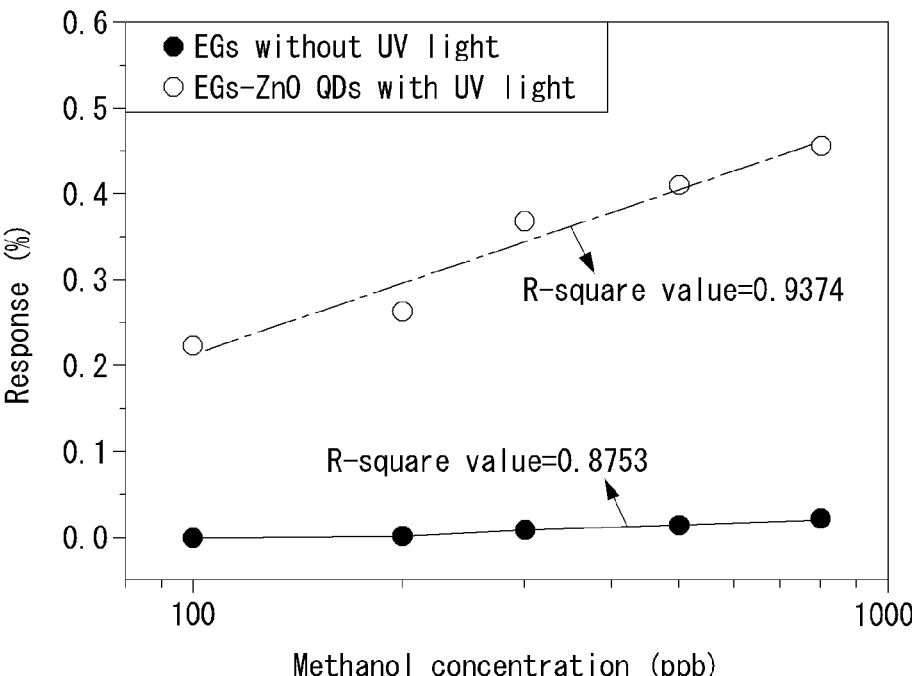

【FIG.32A】
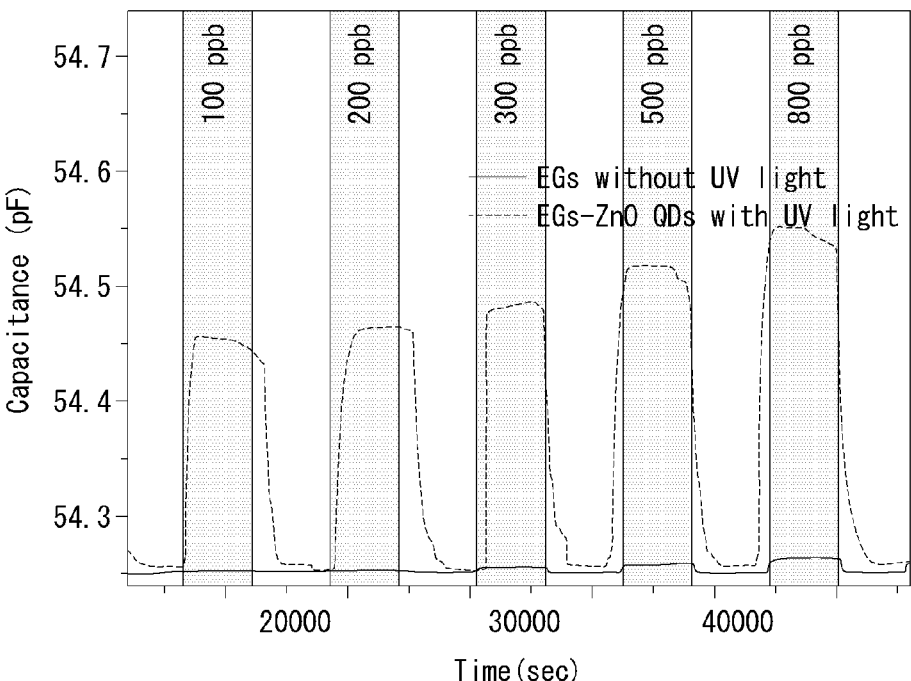
【FIG.32B】
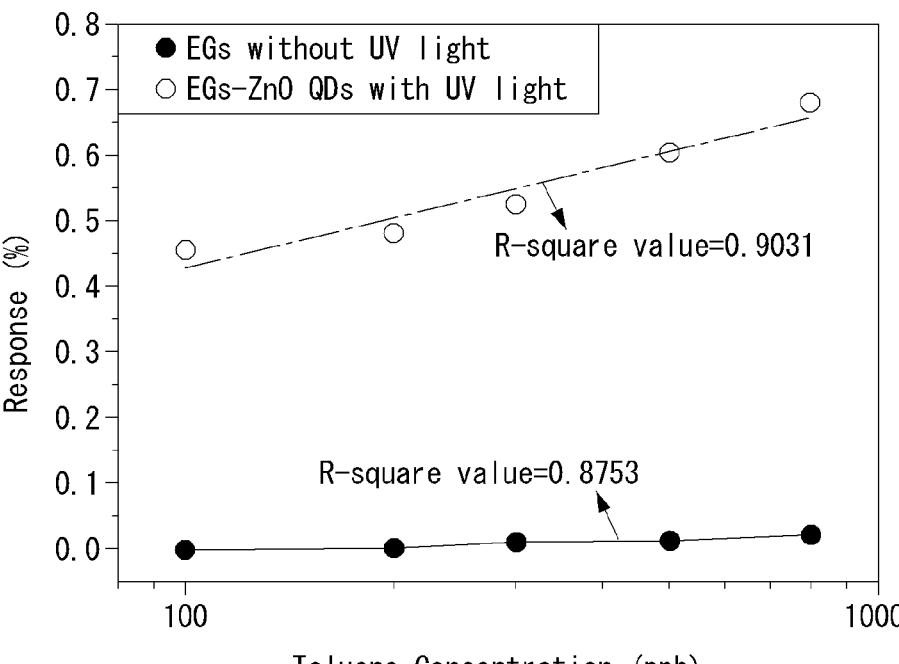

【FIG.33A】
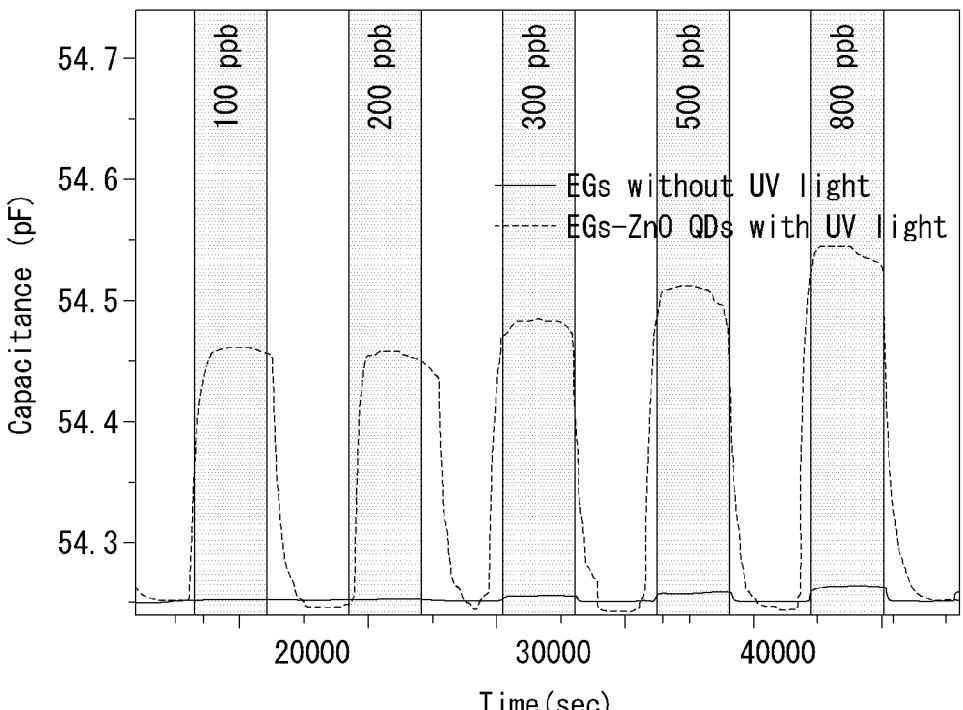
【FIG.33B】
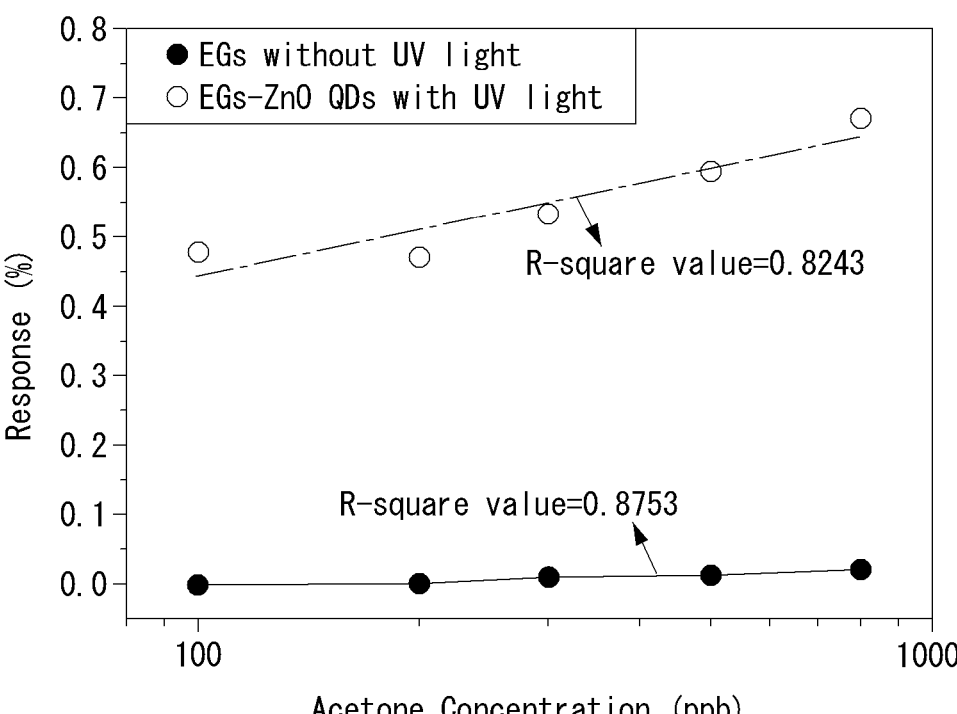

COMPLEX GAS SENSOR, METHOD FOR MANUFACTURING SAME, AND METHOD FOR CONTROLLING COMPLEX GAS SENSOR

CROSS REFERENCE TO RELATED APPLICATIONS

This application is a U.S. National Stage Application of International Application No. PCT/KR2022/007733, filed on May 31, 2022, which claims the benefit under 35 USC 119 (a) and 365(b) of Korean Patent Application No. 10-2022-0016626, filed on Feb. 9, 2022, No. 10-2022-0052559, filed on Apr. 28, 2022, and No. 10-2022-0052560, filed on Apr. 28, 2022, in the Korean Intellectual Property Office, the entire disclosures of which are incorporated herein by reference for all purposes.

BACKGROUND

1. Field of the Invention

The present disclosure relates to a complex gas sensor, a manufacturing method thereof, and a method of controlling the complex gas sensor, and more particularly, to a complex gas sensor configured to detect a target gas using changes in optical energy and capacitance, a manufacturing method thereof, and a method of controlling the complex gas sensor.

2. Discussion of Related Art

Recently, with the increase in interest in environmental pollution and health, the need for detection of various harmful gases has increased significantly. Gas sensors are in high demand because they are required in the entire industrial field of health, environment, agriculture, and defense. Accordingly, the gas sensors will become essential tools for the realization of a future society with improved human living conditions, and harmful gases in the environment are required to be measured and controlled more accurately.

In order for these gas sensors to be practical, the gas sensors need to be highly sensitive, highly selective, highly stable, and highly responsive, and also need to be low power consumption and highly integrated. In order to meet these requirements, the gas sensors are being developed and researched using various sensor structures and materials. Resistive gas sensors based on oxide semiconductors such as tin oxide ($SnO_2$), tungsten oxide ($WO_3$), and zinc oxide (ZnO) can achieve high sensitivity, but are highly affected by temperature, humidity, and an external environment due to structural reasons. In addition, the resistive gas sensors are unstable in contact resistance, have trouble measuring other types of gases, and have low selectivity, reproducibility, and long-term stability due to surface contamination. Further, since the resistive gas sensors operate at high temperatures, a heater is essential, which increases the power consumption of the sensor itself.

Accordingly, various technologies related to complex gas sensors, which are distinguished from the resistive gas sensors, are being developed. For example, Korean Patent Registration No. 10-1201896 (Application No.: 10-2009-0025688, Applicant: Electronics and Telecommunications Research Institute) discloses a capacitive type environmentally harmful gas sensor including an insulating substrate, a metal electrode and a micro-thin film heater heating wire integrally formed on the same plane of the insulating substrate, and an oxide sensing layer formed by being coated on the metal electrode and the micro-thin film heater heating wire and composed of composite oxide thin film or composite oxide nanofiber of nanocrystals in which a P-type oxide semiconductor and an N-type oxide semiconductor are mixed.

SUMMARY OF THE INVENTION

The present disclosure is directed to providing a complex gas sensor capable of being driven at room temperature and a manufacturing method thereof.

Also, the present disclosure is directed to providing a complex gas sensor with an improved response speed and recovery speed and a manufacturing method thereof.

Also, the present disclosure is directed to providing a complex gas sensor capable of selectively sensing any one of methanol gas, toluene gas, and acetone gas, and a manufacturing method thereof.

Also, the present disclosure is directed to providing a complex gas sensor in which noise due to a phase difference is reduced, and a manufacturing method thereof.

Also, the present disclosure is directed to providing a complex gas sensor with increased response and concentration linearity through irradiation from a light source, and a manufacturing method thereof.

The technical problems to be solved by the present disclosure are not limited to those described above.

To solve the above-described technical problems, the present disclosure provides a complex gas sensor.

The complex gas sensor according to one embodiment may include a light source configured to irradiate light, and a gas detection part in which adsorption of a target gas is promoted by the light and whose capacitance changes according to the adsorption of the target gas.

According to one embodiment, the gas detection part may include a sensitive part configured to adsorb and desorb the target gas, a top electrode surrounding the sensitive part, a bottom electrode facing the top electrode, and a porous structure disposed between the top electrode and the bottom electrode.

According to one embodiment, in the sensitive part, a polarization phenomenon may occur by light energy irradiated from the light source, and the adsorption of the target gas may be promoted by the polarization phenomenon.

According to one embodiment, in the gas detection part, a frequency of a voltage applied to the top electrode and the bottom electrode may be differently controlled according to a type of the target gas.

According to one embodiment, the target gas may include any one of methanol gas, toluene gas, and acetone gas, and any one of the methanol gas, the toluene gas, and the acetone gas may be selectively sensed according to the frequency of the voltage applied to the top electrode and the bottom electrode.

According to one embodiment, the porous structure may include any one of anodic aluminum oxide (AAO), silicon oxide ($SiO_2$), polyimide (PI), polyethylene terephthalate (PET), polyethylene naphthalate (PEN), and polytetrafluoroethylene (PTFE).

According to one embodiment, the sensitive part may include a sensitive material including functional groups including a carboxyl group (—COOH) and a hydroxyl group (—OH). Here, the sensitive part may include any one of graphene, carbon nanotube (CNT), amorphous carbon, active carbon, and biochar as a sensitive material.

According to one embodiment, the light source may emit light a wavelength of an ultraviolet region, and, in the sensitive part, a polarization phenomenon may occur by absorbing the ultraviolet light, and the adsorption of the target gas is promoted according to the polarization phenomenon.

According to one embodiment, the complex gas sensor may further include a control part configured to control a frequency of a voltage applied to the gas detection part to be greater than 800 Hz and less than 3,000 Hz, and sense toluene gas on the basis of the change in capacitance of the gas detection part.

According to one embodiment, the complex gas sensor may further include a control part configured to control a frequency of a voltage applied to the gas detection part to be 300 Hz or more and 800 Hz or less, and sense acetone gas on the basis of the change in capacitance of the gas detection part.

According to one embodiment, the complex gas sensor may further include a control part configured to control a frequency of a voltage applied to the gas detection part to be 10 kHz or more and 1 MHz or less, and sense methanol gas on the basis of the change in capacitance of the gas detection part.

A method of manufacturing a complex gas sensor according to the one embodiment may include providing a gas detection part, preparing a porous structure, forming a top electrode on an upper surface of the porous structure such that one region of the upper surface of the porous structure is exposed, forming a bottom electrode on a lower surface of the porous structure, forming a sensitive part configure to adsorb and desorb a target gas in the exposed region of the upper surface of the porous structure, and providing a light source configured to irradiate light to at least a portion of the sensitive part.

In addition, the forming of the sensitive part may include preparing a sensitive material in which the adsorption of the target gas is promoted by light energy irradiated from the light source, preparing a source solution by mixing a solvent with the sensitive material, and providing the source solution to the exposed region of the upper surface of the porous structure while the porous structure is heat-treated.

A method of controlling a complex gas sensor including a light source and a gas detection part of which capacitance changes according to adsorption of a target gas may include irradiating light to the gas detection part by controlling the light source, applying a voltage having a detection frequency to the gas detection part, detecting the change in capacitance of the gas detection part, and sensing the target gas on the basis of the change in capacitance Here, the applying of the voltage having the detection frequency to the gas detection part may further include determining the detection frequency according to a type of the target gas to be detected.

In addition, the sensing of the target gas may further include sensing the target gas when the change in capacitance exceeds a preset reference.

To solve the above-described technical problems, the present disclosure also provides a complex gas sensor including a light source configured to irradiate light, and a gas detection part of which capacitance changes according to adsorption of a target gas, wherein the gas detection part may include a sensitive composite including a sensing part configured to adsorb the target gas and a photo-active part configured to promote the adsorption of the target gas of the sensing part by light energy supplied from the light source, a top electrode surrounding the sensitive composite, a bot-tom electrode facing the top electrode, and a porous structure disposed between the top electrode and the bottom electrode.

To solve the above-described technical problems, the present disclosure also provides a method of manufacturing a complex gas sensor, the method including preparing a porous structure, forming a top electrode on an upper surface of the porous structure such that one region of the upper surface of the porous structure is exposed, forming a bottom electrode on a lower surface of the porous structure, forming, in the exposed region of the upper surface of the porous structure, a sensitive composite including a sensing part configured to adsorb and desorb a target gas and a photo-active part configured to promote the adsorption of the target gas, and providing a light source configured to irradiate light to at least a portion of the sensitive composite.

To solve the above-described technical problems, the present disclosure also provides a method of controlling a complex gas sensor including a light source and a gas detection part of which capacitance changes according to adsorption of a target gas, the method including irradiating light to the gas detection part by controlling the light source, applying a voltage having a detection frequency to the gas detection part, detecting a change in capacitance of the gas detection part, and sensing the target gas on the basis of the change in capacitance.

BRIEF DESCRIPTION OF THE DRAWINGS

FIG. 1 is a view schematically illustrating a structure of a gas sensor according to one embodiment of the present disclosure;

FIG. 2 is a view schematically illustrating a structure of a gas detection part of the gas sensor according to one embodiment of the present disclosure;

FIG. 3A schematically illustrates a top electrode of the gas sensor according to one embodiment of the present disclosure, and FIG. 3B schematically illustrates a bottom electrode of the gas sensor according to one embodiment of the present disclosure.

FIG. 4 illustrates a top image and a bottom image of the gas sensor according to one embodiment of the present disclosure;

FIG. 5 is a flowchart illustrating a method of manufacturing the gas sensor according to one embodiment of the present disclosure;

FIG. 6 is a flowchart for describing a method of manufacturing the gas detection part of the gas sensor according to one embodiment of the present disclosure;

FIGS. 7A to 7C are views illustrating a detection method of the gas sensor according to one embodiment of the present disclosure;

FIG. 8 is a flowchart illustrating a control method of the gas sensor according to one embodiment of the present disclosure;

FIG. 9 is a view schematically illustrating a structure of a gas sensor according to another embodiment of the present disclosure;

FIG. 10 is an exploded view schematically illustrating a structure of a gas detection part of the gas sensor according to another embodiment of the present disclosure;

FIG. 11 is a flowchart for describing a method of manufacturing the gas detection part of the gas sensor according to another embodiment of the present disclosure;

FIG. 12 is a graph comparing electrical characteristics of gas sensors according to Examples and Comparative Example of the present disclosure;

FIG. 13 is an image of a sensitive part included in the gas sensor according to the embodiment of the present disclosure;

FIG. 14A is a result of X-ray diffraction (XRD) analysis of the sensitive part according to one embodiment, and FIG. 14B is a Raman spectroscopy result of the sensitive part according to one embodiment;

FIG. 15 is a result of Fourier-transform infrared spectroscopy (FT-IR) analysis of the sensitive part according to one embodiment;

FIG. 16 is a result of UV-visible spectrum analysis of the sensitive part according to one embodiment;

FIGS. 17A and 17B are graphs illustrating methanol gas sensing characteristics according to frequency of the gas sensor manufactured according to the embodiment of the present disclosure;

FIGS. 18A and 18B are graphs illustrating toluene gas sensing characteristics according to frequency of the gas sensor manufactured according to the embodiment of the present disclosure;

FIGS. 19A and 19B are graphs illustrating acetone gas sensing characteristics according to frequency of the gas sensor manufactured according to the embodiment of the present disclosure;

FIG. 20 is a graph comparing gas sensing characteristics according to frequency of the gas sensor manufactured according to the embodiment of the present disclosure;

FIG. 21 is a graph illustrating sensitivity according to a concentration of gas provided to the gas sensor according to the embodiment of the present disclosure;

FIG. 22 is a graph illustrating a response time according to the concentration of gas provided to the gas sensor according to the embodiment of the present disclosure;

FIG. 23 is a graph illustrating a recovery time according to the concentration of gas provided to the gas sensor according to the embodiment of the present disclosure;

FIGS. 24A and 24B are graphs showing methanol gas detection characteristics of the gas sensor using photo-active energy according to one embodiment of the present disclosure;

FIGS. 25A and 26B are graphs showing toluene gas detection characteristics of the gas sensor using photo-active energy according to one embodiment of the present disclosure;

FIGS. 26A and 26B are graphs showing acetone gas detection characteristics of the gas sensor using photo-active energy according to one embodiment of the present disclosure;

FIG. 27 is a result of XRD analysis of the sensitive part according to one embodiment;

FIG. 28 is an image of a sensitive composite included in a gas sensor according to another embodiment of the present disclosure;

FIGS. 29A and 29B are results of analyzing the sensitive composite according to one embodiment according to an X-ray photoelectron spectroscopy (XPS) method;

FIGS. 30A and 30B are graphs showing optical characteristics of a ZnO quantum dot, which is an active material;

FIGS. 31A and 31B are graphs showing methanol gas detection characteristics of the gas sensor according to another embodiment of the present disclosure;

FIGS. 32A and 32B are graphs showing toluene gas detection characteristics of the gas sensor according to another embodiment of the present disclosure; and FIGS. 33A and 33B are graphs showing acetone gas detection characteristics of the gas sensor according to another embodiment of the present disclosure.

6

DETAILED DESCRIPTION OF THE EMBODIMENTS

Hereinafter, embodiments of the present disclosure will be described in detail so that those of ordinary skill in the art can easily carry out the present disclosure. However, the present disclosure may be implemented in various different forms and is not limited to the embodiments described below.

In the present specification, when a component is referred to as being on another component, the component may be directly formed on another component or a third component may be interposed between the component and the other component. In addition, in the drawings, thicknesses of a film and a region are exaggerated to effectively describe technical contents.

Further, while the terms such as a first, a second, a third, and the like are used to describe various components in various embodiments of the present specification, these components should not be limited to these terms. These terms are used only to distinguish one component from another component. Accordingly, a first component as being referred in any one embodiment may be referred to as a second component in another embodiment. Each embodiment described and exemplified herein also includes a complementary embodiment. In addition, in present specification, the term "and/or" is used to mean at least one of components listed before and after.

A singular expression in the specification includes a plurality of expressions unless the context clearly indicates otherwise. Further, the terms "including," "having," or the like are used to specify that a feature, a number, a step, a component, or a combination thereof described herein exists, and they do not preclude the presence or addition of one or more other features, numbers, steps, components, or combinations thereof. In addition, in the present specification, the term a "connection" is used to mean including both indirectly and directly connecting a plurality of components.

Further, in the following description of the present disclosure, when a detailed description of related known configurations or functions is determined to unnecessarily obscure the gist of the present disclosure, the detailed description thereof will be omitted.

The advantages and features of the present disclosure and ways to achieve them will be apparent by making reference to embodiments as described below in detail in conjunction with the accompanying drawings. However, the present disclosure is not limited to the embodiments set forth below, but may be implemented in various different forms. The following embodiments are provided only to completely disclose the present disclosure and inform those skilled in the art of the scope of the present disclosure, and the present disclosure is defined only by the scope of the appended claims.

FIG. 1 is a view schematically illustrating a structure of a complex gas sensor 10 according to one embodiment of the present disclosure.

Referring to FIGS. 1 and 2, the complex gas sensor 10 according to one embodiment may include a gas detection part 200 whose capacitance changes according to adsorption and desorption of a target gas, a light source 100 configured to irradiate light to the gas detection part 200, and a control part 300 configured to sense the target gas on the basis of a change in capacitance of the gas detection part 200.

Here, the target gas may be a hazardous, toxic, or dangerous gas that needs to be detected. In one embodiment, the target gas may include any one of methanol gas, toluene gas, and acetone gas, and in another embodiment, the target gas may be a volatile organic compounds (VOCs) gas.

The light source 100 irradiates the gas detection part 200 with light. Specifically, the light source 100 is provided such that light is irradiated to at least a portion of a sensitive part 240 to be described below, and supplies light energy to the sensitive part 240. The light irradiated from the light source 100 increases active energy of the sensitive part 240, and thus the light source 100 provides photo-active energy to the sensitive part 240.

Preferably, the light source 100 may be provided such that light is irradiated to the entire sensitive part 240, and may be provided to have a predetermined distance from the gas detection part 200 as necessary. The light source 100 may be one of a point light source 100, a linear light source 100, and a surface light source 100.

The light source 100 emits a light wavelength in the ultraviolet region. The light source 100 may include an ultraviolet lamp, a diode (a light-emitting diode (LED)), or the like. The light source 100 according to one embodiment may emit light of a wavelength between 200 nm and 400 nm in which an absorption peak of the sensitive part 240 is the greatest.

That is, the light irradiated from the light source 100 to the gas detection part 200 supplies photo-active energy to the gas detection part 200. Due to such photo-active energy, the adsorption and desorption of the target gas of the gas detection part 200 are promoted. Thus, it is to be understood that target gas detection sensitivity of the complex gas sensor 10 including the light source 100 is further increased.

The gas detection part 200 includes a porous structure 210 and a plurality of electrodes, and changes in capacitance as the target gas is coupled thereto. In order to easily measure the change in capacitance of the gas detection part 200, the porous structure 210 may be made of a material having a low permittivity.

The control part 300 adjusts a frequency of a voltage applied to the gas detection part 200, and senses the target gas by detecting a capacitance varying according to the adsorption and desorption of the target gas. At this time, the control part 300 may adjust the frequency of the voltage applied to the electrode according to the target gas to be sensed. A proper frequency changed according to the target gas as described above is referred to as a detection frequency.

In addition, the control part 300 may control light irradiation of the light source 100. The control part 300 controls on/off of the light source 100, and may minimize power consumption of the sensor by turning the light source 100 off when not detecting gas and turning the light source 100 on when detecting gas.

Hereinafter, the gas detection part 200 will be described in more detail with reference to the drawings. FIG. 2 is a view schematically illustrating a structure of the gas detection part 200 of the complex gas sensor 10 according to one embodiment of the present disclosure, FIG. 3 schematically illustrates the electrode of the complex gas sensor 10 according to one embodiment of the present disclosure, and FIG. 4 illustrates a top image and a bottom image of the complex gas sensor 10 according to one embodiment of the present disclosure.

Referring to FIG. 2, the gas detection part 200 includes a top electrode 220, a bottom electrode 230 provided to face the top electrode 220, the porous structure 210 provided between the top electrode 220 and the bottom electrode 230, and the sensitive part 240 provided adjacent to the top electrode 220 and the porous structure 210.

In order to easily measure a change in capacitance, the porous structure 210 may be made of a material having a low permittivity.

The porous structure is provided between the top electrode 220 and the bottom electrode 230, and when a voltage is applied to the top electrode 220 and the bottom electrode 230, electric charges are charged to the porous structure according to permittivity. That is, when the voltage is applied to the top electrode 220 and the bottom electrode 230, the porous structure 210 has a capacitance directly proportional to the permittivity.

According to one embodiment, the porous structure 210 may include any one of anodic aluminum oxide (AAO), silicon oxide ($SiO_2$), polyimide (PI), polyethylene terephthalate (PET), polyethylene naphthalate (PEN), and polytetrafluoroethylene (PTFE), but the porous structure 210 may be any material as long as it has a low permittivity and is easy to observe a change in capacitance.

In the following description of the complex gas sensor 10 according to the embodiment of the present disclosure, a case in which the porous structure 210 is anodic aluminum oxide is exemplarily described.

The top electrode 220 may be provided on one surface of the porous structure 210 and may be electrically connected to the bottom electrode 230. The bottom electrode 230 may be formed on another one surface of the porous structure 210 different from the one surface on which the top electrode 220 is provided.

The top electrode 220 and the bottom electrode 230 may each include a metal. For example, the top electrode 220 and the bottom electrode 230 may each include gold (Au), and the top electrode 220 and the bottom electrode 230 may be electrically connected to each other.

The top electrode 220 is located on one surface (hereinafter, an upper surface) of the porous structure 210 facing the light source 100. The top electrode 220 may be provided only on a portion of one surface of the porous structure 210 to expose one region of the upper surface of the porous structure 210. For example, the top electrode 220 may have a ring shape with a hollow formed at its central portion. In this case, one region of the upper surface of the porous structure 210 may be exposed through the hollow formed in the central portion of the top electrode 220.

The top electrode 220 and the bottom electrode 230 may be provided in different forms from those shown in FIG. 3. The top electrode 220 according to one embodiment may have a ring shape as shown in FIG. 3A. Alternatively, the bottom electrode 230 may have a circle plate shape as shown in FIG. 3B. Accordingly, sensing sensitivity may be improved since noise caused by a phase difference between the top electrode 220 and the bottom electrode 230 is reduced, so that driving may be easily performed at room temperature.

The sensitive part 240 is provided on one surface of the porous structure 210, and adsorbs and desorbs the target gas. The sensitive part 240 may be provided on one surface of the porous structure 210 facing the light source 100 in the same manner as the top electrode 220.

The sensitive part 240 may be integrally formed with the above-described top electrode 220 and may be provided on the porous structure 210 together with the top electrode 220. To this end, one region in which the sensitive part 240 is to be formed may be provided in the top electrode 220, and the sensitive part 240 may be provided in a region in which the top electrode 220 is not provided. For example, as shown in FIG. 3A, when the top electrode has a shape of a ring, the sensitive part 240 may be provided at a central portion of the ring.

The sensitive part 240 may be provided on one surface of the top electrode 220, and may adsorb and desorb the target gas. A polarization phenomenon is accelerated in the sensitive part 240 by the light energy irradiated from the light source 100, and thus the adsorption of the target gas may be further promoted.

The target gas adsorbed to and desorbed from the sensitive part 240 may include any one of methanol gas, toluene gas, and acetone gas, and according to another embodiment, the target gas may be a volatile organic compounds (VOCs) gas.

The sensitive part 240 may include a sensitive material that adsorbs and desorbs the target gas. Here, the sensitive material may be stacked in a nanometer scale to form the sensitive part 240.

The capacitance of the gas detection part 200 may be changed when a sensitive material SM adsorbs and desorbs the target gas. Accordingly, the target gas may be sensed by measuring the change in capacitance of the gas detection part 200.

The permittivity of the sensitive material changes according to the adsorption or desorption of the target gas. The sensitive material may be a material having a low permittivity in consideration of a sensitivity of the target gas according to the change in capacitance.

As described above, a response speed and a recovery speed may be improved by using a sensitive material whose permittivity changes according to the adsorption or desorption of the target gas.

In addition, the sensitive material may adsorb and desorb the target gas through a functional group. Specifically, the sensitive material may include a carboxyl group (—COOH) and a hydroxyl group (—OH) as functional groups in order to adsorb and desorb the target gas.

When graphene is used as the sensitive material, adsorption and desorption performance of the target gas may be improved by π-bonding of the functional group and the graphene. As a result, the response speed and recovery speed of the complex gas sensor 10 may be improved.

In addition, the polarization phenomenon of the sensitive material may be accelerated by the photo-active energy. When light is irradiated from the light source 100, a polarization phenomenon occurs in the sensitive material absorbing the light energy, and the adsorption of the target gas is promoted by the polarization phenomenon of the sensitive material.

In order to increase an adsorption promoting effect of the target gas according to light irradiation, the light source 100 that generates a wavelength matching a light absorption wavelength of the sensitive material may be selected The sensitive material according to one embodiment may have a high absorption rate of light at a wavelength of 200 nm to 400 nm, and accordingly, the light source 100 emitting ultraviolet light corresponding to a wavelength between 200 nm and 400 nm may be selected.

The sensitive material SM according to one embodiment may include any one of graphene, carbon nanotube (CNT), amorphous carbon, active carbon, and biochar. In addition, any material that adsorbs and desorbs the target gas, changes the permittivity of the porous structure 210, and absorbs the light irradiated from the light source 100 may be used as the sensitive material.

When graphene is used as the sensitive material, the graphene may have a relatively high surface area due to two-dimensional characteristics of the graphene. Accordingly, sensing characteristics of the complex gas sensor 10 to be described below may be improved as an adsorption area of the target gas is relatively increased.

In addition, the graphene may include a carboxyl group (—COOH) and a hydroxyl group (—OH) to adsorb and desorb the target gas. When the graphene is used as the sensitive material, the adsorption and desorption performance of the target gas may be improved by the π-bonding of the functional group and the graphene. Accordingly, the response speed and recovery speed of the complex gas sensor 10 to be described below may be improved.

As shown in FIG. 4, in the complex gas sensor 10 according to one embodiment, the top electrode 220 may have a ring shape, the bottom electrode 230 may have a circle plate shape, and the top electrode 220 and the sensitive part 240 may be integrally formed.

That is, the complex gas sensor 10 according to the embodiment of the present disclosure may include the sensitive part 240 configured to adsorb and desorb the target gas (for example, volatile organic compounds gas such as methanol gas, toluene gas, acetone gas, and the like), the top electrode 220 surrounding the sensitive part 240, the bottom electrode 230 facing the top electrode 220, and the porous structure 210 (for example, anodic aluminum oxide) disposed between the top electrode 220 and the bottom electrode 230, wherein the capacitance is changed as the sensitive material SM adsorbs and desorbs the target gas. Accordingly, the complex gas sensor 10 having improved response speed and recovery speed may be provided.

FIG. 5 is a flowchart illustrating a method of manufacturing the complex gas sensor 10 according to one embodiment of the present disclosure.

A gas detection part 200 is provided (S10). A specific manufacturing method of the gas detection part 200 will be described below. The providing of the gas detection part 200 may further include electrically connecting a top electrode 220 and a bottom electrode 230 of the gas detection part 200 to a power supply and a control part 300. The connection method would be obvious to those skilled in the art, and thus a detailed description thereof will be omitted.

A light source 100 is provided so that light is irradiated to the gas detection part 200 (S20). The light source 100 may be provided to irradiate the gas detection part 200 with light, and specifically, and may be provided so that the light is irradiated to at least a portion of a sensitive part 240 included in the gas detection part 200. Here, the light source 100 may be provided to be spaced apart from the gas detection part 200 by a preset distance.

Hereinafter, the method of manufacturing the gas detection part 200 will be described in detail with reference to the accompanying drawings. FIG. 6 is a flowchart for describing the method of manufacturing the gas detection part 200 of the complex gas sensor 10 according to one embodiment of the present disclosure. FIG. 7 is a view illustrating a detection method of the complex gas sensor 10 according to one embodiment of the present disclosure.

Referring to FIGS. 6 and 7, a porous structure 210 may be prepared as illustrated in FIG. 7A (S100). According to one embodiment, the porous structure 210 may be manufactured with any one of anodic aluminum oxide (AAO), silicon oxide ($SiO_2$), polyimide (PI), polyethylene terephthalate (PET), polyethylene naphthalate (PEN), and polytetrafluoroethylene (PTFE).

As shown in FIG. 7B, a top electrode 220 is formed on one surface of the porous structure 210 (S110). The top electrode 220 may be made of a metal. At this time, the top electrode 220 may be provided only on a portion of an upper surface of the porous structure 210, may preferably be provided in a ring shape with a hollow formed in the center.

Various electrode forming methods may be used to form the top electrode 220. For example, the top electrode 220 may be formed by a gold (Au)-electrode sputtering method, and may be manufactured using a mask having a shape of a circle to form a space in which the sensitive part 240 is to be provided.

As shown in FIG. 7B, a bottom electrode 230 may be formed on another one surface of the porous structure 210 (S120). The bottom electrode 230 may be made of a metal on one surface different from the one surface on which the top electrode 220 is provided. For example, the metal may include gold (Au).

The bottom electrode 230 is not limited in shape and size, but may preferably be provided in a shape facing that of the top electrode 220, thereby reducing noise caused by a phase difference between the top electrode 220 and the bottom electrode 230.

Various electrode forming methods may be used to form the bottom electrode 230. For example, the bottom electrode 230 may be formed by a gold (Au)-electrode sputtering method, and may be manufactured using a mask having a ring shape in order to be manufactured in a shape facing that of the top electrode 220.

As shown in FIG. 7C, a sensitive part 240 may be formed on one surface of the porous structure 210 (S130). The sensitive part 240 may be formed on one surface of the porous structure 210 on which the top electrode 220 is not provided. For example, when the top electrode 220 has a shape of a ring, the sensitive part 240 may be formed in a hollow formed in the center of the ring.

Here, the sensitive part 240 may be formed by coating a sensitive material. Specifically, the forming of the sensitive part 240 may include preparing a source solution in which a sensitive material is mixed with a solvent, applying the source solution on one surface of the porous structure 210, in which the top electrode 220 is not formed, and evaporating the solvent in the source solution through heat treatment.

FIG. 8 is a flowchart illustrating a control method of the complex gas sensor 10 according to one embodiment of the present disclosure.

Referring to FIGS. 1 and 8, the complex gas sensor 10 irradiates light (S310). Specifically, the light source 100 irradiates the gas detection part 200 with the light. At this time, operations of the light source 100 may be controlled by the control part 300, and light irradiation may be performed at regular time intervals in consideration of the efficiency of the complex gas sensor 10.

The complex gas sensor 10 applies a voltage to the electrodes (S320). The voltage is applied to the top electrode 220 and the bottom electrode 230. At this time, the control part 300 may adjust a frequency of the voltage applied to the top electrode 220 and the bottom electrode 230 according to a target gas.

Specifically, the complex gas sensor 10 may control the frequency of the voltage applied to the top electrode 220 and the bottom electrode 230 to be different according to the type of the target gas (for example, any one of methanol gas, toluene gas, and acetone gas). The target gas that the complex gas sensor 10 can detect may be determined according to the frequency of the voltage being controlled, and any one of methanol gas, toluene gas, and acetone gas may be selectively sensed according to the frequency control.

In one embodiment, the control part 300 may sense methanol gas by controlling the frequency of the voltage applied to the top electrode 220 and the bottom electrode 230 to be greater than or equal to 800 kHz and less than or equal to 1 MHz.

In another embodiment, the control part 300 may sense toluene gas by controlling the frequency of the voltage applied to the top electrode 220 and the bottom electrode 230 to be greater than 800 Hz and less than 10 KHz.

In still another embodiment, the control part 300 may sense acetone gas by controlling the frequency of the voltage applied to the top electrode 220 and the bottom electrode 230 to be greater than 300 Hz and less than 800 Hz.

The complex gas sensor 10 detects a change in capacitance (S330). The control part 300 monitors a change in capacitance of the gas detection part 200 when a voltage is applied to the top electrode 220 and the bottom electrode 230.

When the voltage is applied to the top electrode 220 and the bottom electrode 230, electric charges are accumulated in the gas detection part 200 to change the capacitance. Since the capacitance is changed according to the permittivity of the porous structure 210 located between the top electrode 220 and the bottom electrode 230, the capacitance of the gas detection part 200 may vary according to the material constituting the porous structure 210 even when the voltage of the same frequency is applied.

Since the frequency of the voltage applied to the top electrode 220 and the bottom electrode 230 acts as a resonance frequency of the gas detection part 200, the capacitance of the gas detection part 200 may vary according to the frequency applied to the top electrode 220 and the bottom electrode 230.

In addition, the capacitance of the gas detection part 200 is affected by the sensitive part 240 adjacent to the porous structure 210. Accordingly, the capacitance may vary according to permittivity of a constituent material of the sensitive part 240.

As described above, the sensitive part 240 includes a sensitive material that adsorbs and desorbs the target gas. When the target gas is introduced into the complex gas sensor 10, the target gas is adsorbed to the sensitive material, thereby changing the permittivity of the sensitive material. When the change in permittivity of the sensitive material occurs, the capacitance measured by the gas detection part 200 changes.

On the contrary, when the target gas is removed from the complex gas sensor 10, desorption of the target gas adsorbed to the sensitive material occurs, and accordingly, the permittivity of the sensitive material changes to change the capacitance.

In addition, as described above, when photo-active energy of the sensitive material is increased by the light energy, since a polarization phenomenon of the sensitive material is accelerated to promote the adsorption of the target gas, the change in capacitance of the complex gas sensor 10 is further increased through the irradiation of the light, and thus the target gas may be detected with a higher sensitivity.

The complex gas sensor 10 detects the target gas (S340). The control part 300 detects that the target gas has been introduced when the capacitance of the gas detection part 200 deviates from a preset reference range. Here, it should be understood that the preset reference range may be determined according to the type of the target gas or may vary according to the resonant frequency of the voltage applied to the electrode.

Meanwhile, although the control method of detecting one target gas has been described in FIG. 8, the gas sensor may detect multiple target gases.

To this end, a plurality of target gases can be detected using a single complex gas sensor by a method of changing a detection frequency applied to the gas detection part at a predetermined time interval and then detecting the capacitance change again.

For example, the complex gas sensor senses methanol gas by monitoring a change in capacitance of the gas detection part by applying a voltage having a frequency greater than or equal to 800 kHz and less than or equal to 1 MHz. In addition, after a predetermined time has elapsed, the frequency of the voltage applied to the gas detection part is changed to be greater than 800 Hz and less than 10 kHz, and the change in capacitance according thereto is monitored to sense toluene gas. After the toluene gas is sensed, the frequency of the voltage applied to the gas detection part is changed to be greater than 300 Hz and less than 800 Hz, and the change in capacitance according thereto is monitored to sense acetone gas. As described above, various types of target gases may be sensed using one sensor while changing the frequency of the voltage applied to the gas detection part step by step.

FIG. 9 is a view schematically illustrating a structure of a complex gas sensor 20 according to another embodiment of the present disclosure. FIG. 10 is an exploded view schematically illustrating a structure of a gas detection part 201 of the complex gas sensor 20 according to another embodiment of the present disclosure.

Referring to FIGS. 9 and 10, the complex gas sensor 20 according to another embodiment may include the gas detection part 201 whose capacitance changes according to adsorption and desorption of a target gas, a light source 100 configured to irradiate light to the gas detection part 201, and a control part 300 configured to sense the target gas on the basis of a change in capacitance.

Hereinafter, for convenience of description, configurations that are identical to those of one embodiment are given identical reference symbols, and descriptions thereof will be omitted. Accordingly, it should be understood that configurations in which the same name or symbol as one embodiment is used in another embodiment are the same as that of one embodiment unless otherwise specified.

The gas detection part 201 according to another embodiment includes a top electrode 220, a bottom electrode 230 provided to face the top electrode 220, a porous structure 210 provided between the top electrode 220 and the bottom electrode 230, and a sensitive composite 280 provided adjacent to the porous structure 210.

The sensitive composite 280 is provided on one surface of the porous structure 210, and adsorbs and desorbs the target gas. The sensitive composite 280 may be provided on one surface of the porous structure 210 facing the light source 100 in the same manner as the top electrode 220.

The sensitive composite 280 is integrally formed with the above-described top electrode 220 and may be provided on the porous structure 210 together with the top electrode 220. To this end, one region in which the sensitive composite 280 is to be formed may be provided in the top electrode 220, and the sensitive composite 280 may be provided in a region in which the top electrode 220 is not provided. For example, as shown in FIG. 10, when the top electrode has a shape of a ring, the sensitive composite 280 may be provided at a central portion of the ring.

When the light is irradiated from the light source 100, the sensitive composite 280 receives photo-active energy to promote adsorption of the target gas. The target gas adsorbed to and desorbed from the sensitive composite 280 may include any one of methanol gas, toluene gas, and acetone gas, and according to another embodiment, the target gas may be a volatile organic compounds (VOCs) gas.

The sensitive composite 280 may include a sensitive part 240 that adsorbs and desorbs the target gas and a photo-active part 250 that promote the adsorption of the target gas. In the sensitive composite 280, the photo-active part 250 is stacked on the sensitive part 240.

The sensitive part 240 is located in the top electrode 220, and may be provided such that one surface thereof is in contact with the porous structure 210. The sensitive part 240 is the same as the complex gas sensor 20 according to one embodiment, and thus a detailed description thereof is omitted.

The photo-active part 250 is stacked on one surface of the sensitive part 240 and absorbs the light emitted from the light source 100. When light energy is absorbed, the photo-active part 250 accelerates a polarization phenomenon of the sensitive part 240 by accelerating polarization of the sensitive material. As such, the adsorption of the target gas of the sensitive part 240 is promoted by the acceleration of the polarization phenomenon of the sensitive part 240.

The photo-active part 250 may include an active material that accelerates the polarization of the sensitive part 240 when the light is absorbed. The active material absorbs the light emitted from the light source 100 and uses the absorbed light energy to accelerate polarization of a surface of the sensitive part 240. As such, the adsorption of the target gas of the sensitive part 240 is promoted according to the acceleration of the polarization of the active material.

The active material according to one embodiment may be a quantum dot (QD) that accelerates the polarization by the light energy. As described above, when the light source 100 emits light in the ultraviolet region, an active material having a high absorption rate of light at a wavelength corresponding to the ultraviolet region may be selected. The active material may be a ZnO quantum dot having a high absorption rate of light at a wavelength of 200 nm to 400 nm irradiated from the light source 100.

Hereinafter, a description is made by assuming that the active material is a ZnO quantum dot, but it should be understood that any material that has a high light absorption rate and can promote the polarization phenomenon in the sensitive part 240 according to the photo-active energy may be selected as the active material.

As such, when the adsorption of the target gas is promoted by the acceleration of the polarization phenomenon by the active material, the change in capacitance proceeds linearly and rapidly, so that the sensitivity of the complex gas sensor 20 may be improved. The improvement of sensitivity and the securing of linearity will be described in more detail in Experimental Example 7.

Meanwhile, although it has been described that the sensitive composite 280 is provided in a form in which the sensitive part 240 for adsorbing and desorbing the target gas and the photo-active part 250 for enhancing optical characteristics are stacked, the sensitive composite 280 may be provided in a form in which a sensitive material and a quantum dot are mixed.

A method of manufacturing the complex gas sensor 20 according to another embodiment is different from the method of manufacturing the gas detection part 201 according to one embodiment only in a gas detection method.

Hereinafter, a method of manufacturing the gas detection part 201 of the complex gas sensor 20 according to another embodiment will be described with reference to the drawings.

FIG. 11 is a flowchart for describing the method of manufacturing the gas detection part 201 of the complex gas sensor 20 according to another embodiment of the present disclosure.

Referring to FIGS. 10 and 11, a porous structure 210 may be prepared (S410). According to one embodiment, the porous structure 210 may be manufactured with any anodic aluminum oxide (AAO), silicon oxide ($SiO_2$), polyimide (PI), polyethylene terephthalate (PET), polyethylene naphthalate (PEN), and polytetrafluoroethylene (PTFE).

A top electrode 220 is formed on one surface of the porous structure 210 (S420). The top electrode 220 may be made of a metal. At this time, the top electrode 220 may be provided only on a portion of an upper surface of the porous structure 210, and may preferably be provided in a ring shape with a hollow formed in the center.

Various electrode forming methods may be used to form the top electrode 220. For example, the top electrode 220 may be formed by a gold (Au)-electrode sputtering method, and may be manufactured using a mask having a shape of a circle to form a space in which the sensitive composite 280 is to be provided.

A bottom electrode 230 may be formed on one surface of the porous structure 210 (S430). The bottom electrode 230 may be made of a metal on one surface different from the one surface on which the top electrode 220 is provided. For example, the metal may include gold (Au).

The bottom electrode 230 is not limited in shape and size, but may preferably be provided in a shape facing that of the top electrode 220, thereby reducing noise caused by a phase difference between the top electrode 220 and the bottom electrode 230.

Various electrode forming methods may be used to form the bottom electrode 230. For example, the bottom electrode 230 may be formed by a gold (Au)-electrode sputtering method, and may be manufactured using a mask having a ring shape in order to be manufactured in a shape facing that of the top electrode 220.

A sensitive composite 280 may be formed on one surface of the porous structure 210 (S440). The sensitive composite 280 may be formed in a region of the porous structure 210 in which the top electrode 220 is not provided. For example, when the top electrode 220 has a shape of a ring, the sensitive composite 280 may be formed in a hollow formed in the center of the ring.

The forming of the sensitive composite 280 may include forming a sensitive part 240 and forming a photo-active part 250.

The sensitive part 240 may be provided by a method of coating a sensitive material on one surface of the porous structure 210 in which the top electrode 220 is provided. Specifically, the forming of the sensitive part 240 may include preparing a source solution in which a sensitive material is mixed with a solvent, applying the source solution on one surface of the porous structure 210, in which the top electrode 220 is not formed, and evaporating the solvent in the source solution through heat treatment.

In addition, the photo-active part 250 may be provided by applying or coating an active material on the sensitive part 240. In one embodiment, zinc acetate dihydrate may be mixed with methylformamide at 1 wt % and heat-treated at 105° C. for 4 hours to manufacture a ZnO quantum dot, and the manufactured quantum dot may be dropped and coated on the sensitive part 240 at room temperature to form the photo-active part 250.

Experimental Example 1: Electrode Structure

In the above, the complex gas sensor 10 of the present disclosure and the method of manufacturing the same have been described. Hereinafter, specific experimental examples of the gas detection part 200 and the manufacturing method thereof and characteristics evaluation results according to the present disclosure will be described.

Manufacture of Gas Detection Part 200 According to Example 1

A porous anodic aluminum oxide template having a diameter of 25 mm and a pore size of 200 nm, and a 0.5 ml source solution in which ethanol and graphene having a concentration of 1.6 wt % are mixed was prepared. The porous anodic aluminum oxide template was placed on a hot plate of 60° C., and then the source solution was provided to an upper surface of the porous anodic aluminum oxide template to form a ring-shaped graphene top electrode 220. In addition, a circle plate-shaped gold (Au) bottom electrode was formed on a lower surface of the porous anodic aluminum oxide template by a sputtering method.

Manufacture of Gas Detection Part 200 According to Example 2

The gas detection part 200 according to Example 1 described above was manufactured, but a porous anodic aluminum oxide template having a diameter of 50 mm was used.

Manufacture of Gas Detection Part 200 According to Comparative Example

A porous anodic aluminum oxide template having a diameter of 25 mm and a pore size of 200 nm was prepared. The gas detection part 200 according to Comparative Example was manufactured by forming a first graphene electrode and a second gold (Al) electrode spaced apart from each other in a horizontal direction on an upper surface of the porous anodic aluminum oxide template.

The features of the gas detection parts 200 according to the above-described Examples and Comparative Example are summarized in Table 1 below.

TABLE 1

| Classification | Electrode structure | Diameter size |
| --- | --- | --- |
| Example 1 | Vertical structure of top electrode 220-bottom electrode 230 | 25 mm |
| Example 2 | Vertical structure of top electrode 220-bottom electrode 230 | 50 mm |
| Comparative Example | Horizontal structure of first electrode-second electrode | 25 mm |

FIG. 12 is a graph comparing electrical characteristics of complex gas sensors 10 by using the gas detection parts 200 according to Examples and Comparative Example of the present disclosure.

Referring to FIG. 12, the complex gas sensor 10 (25 mm AAO_Vertical) according to Example 1, the complex gas sensor 10 (50 mm AAO) according to Example 2, and the complex gas sensor 10 (25 mm AAO_Horizon) according to Comparative Example were prepared, and then methanol gases having concentrations of 5, 10, 20, 50, and 100 ppm were flowed into each of the complex gas sensors 10, and capacitance changes over time are illustrated.

It was confirmed that, in the case of the complex gas sensor 10 according to Comparative Example, a noise signal (signal to noise) was greatly generated, and thus a change in capacitance due to the gas concentration and adsorption and desorption of the methanol gas did not substantially occur as can be seen in FIG. 12. Unlike this, it was confirmed that, in the complex gas sensors 10 according to Examples 1 and 2, noise due to a phase difference between the top electrode 220 and the bottom electrode 230 of a vertical structure was reduced, and thus a change in capacitance due to the gas concentration and adsorption and desorption of the methanol gas occurred. In particular, it was confirmed that the complex gas sensor 10 according to Example 1 had a remarkably fast response speed and recovery speed according to the adsorption and desorption as compared to the complex gas sensor 10 according to Example 2.

Accordingly, it can be seen that the sensing characteristics of the complex gas sensor 10 may be improved by the vertical structure of the top electrode 220 and the bottom electrode 230. In addition, it can be seen that the sensing characteristics of the complex gas sensor 10 may be improved by controlling the diameter of the porous anodic aluminum oxide template to 25 mm.

Experimental Example 2: Characteristics of Sensitive Part 240 of One Embodiment Hereinafter, in one embodiment, characteristics of the sensitive part 240 using graphene as a sensitive material will be described in detail with reference to the accompanying drawings.

FIG. 13 is an image of the sensitive part 240 included in the complex gas sensor 10 according to the embodiment of the present disclosure.

The sensitive part 240 may be formed by stacking a sensitive material in a nanometer scale. FIG. 13 is a transmission electron microscope (TEM) image of the sensitive part 240 manufactured using the graphene as a sensitive material according to one embodiment. Referring to FIG. 13, it is confirmed that the sensitive part 240 has a layered structure of about 6 layers of graphene in which the graphene, which is a sensitive material, is stacked to a thickness of several nanometers.

FIG. 14A is a result of X-ray diffraction (XRD) analysis of the sensitive part 240 according to one embodiment, and FIG. 14B is a Raman spectroscopy result of the sensitive part 240 according to one embodiment.

Referring to FIG. 14A, it was confirmed that a hexagonal phase of carbon (JCPDS number: 26-1077) was formed on the sensitive part 240 included in the complex gas sensor 10. In addition, since other peaks other than carbon were not observed, it was found that the sensitive part 240 was made of high-purity graphene.

Referring to FIG. 14B, since the sensitive part 240 has three peaks corresponding to 1350 $cm^{-1}$ (D band), 1590 $cm^{-1}$ (G band), and 2676 $cm^{-1}$ (2D band), it was found that the sensitive part was made of graphene. Here, the D band represents $sp^3$ bonding carbon, the G band mainly represents the vibration of $sp^2$ bonding carbon, and the 2D band represents the formation of multi-layer graphene.

FIG. 15 is a result of Fourier-transform infrared spectroscopy (FT-IR) analysis of the sensitive part 240 according to one embodiment.

The sensitive material may include a carboxyl group (—COOH) and a hydroxyl group (—OH) as functional groups in order to adsorb and desorb the target gas.

Referring to the FT-IR spectrum of FIG. 15, the peak at 3433 $cm^{-1}$ is an OH vibrational peak, and it can be confirmed that a hydroxyl group (—OH functional group) is abundantly present in the sensitive part 240 according to one embodiment.

In addition, the peak at 1389 $cm^{-1}$ is a C—OH vibration peak, the peaks at 1050 $cm^{-1}$ and 1121 $cm^{-1}$ are C—O vibration peaks, and the peak at 1647 $cm^{-1}$ is a C=O vibration peak. From such vibration peaks, it can be confirmed that the carboxyl group (—COOH) is abundantly present in the sensitive part 240 according to one embodiment.

The sensitive material absorbs the light irradiated from the light source 100. FIG. 16 is a result of UV-visible spectrum analysis of the sensitive part 240 according to one embodiment.

Referring to FIG. 16, it was confirmed that, in the sensitive part 240 according to one embodiment, an absorption peak appeared to be the largest at 270 nm, and decreased as the wavelength increased. That is, the sensitive part 240 according to one embodiment well absorbs light of 200 nm to 400 nm or less, which is an UV region.

Experimental Example 3: Target Gas Selectivity

As described above, the target gas detectable by the complex gas sensor 10 may be selected according to a frequency of a voltage applied to the electrode. Hereinafter, target gas selectivity using a frequency will be described in detail with reference to the accompanying drawings.

FIG. 17 is a graph illustrating methanol gas sensing characteristics according to frequency of the complex gas sensor 10 manufactured according to the embodiment of the present disclosure.

The complex gas sensor 10 manufactured according to Example 1 was stabilized by flowing dry air gas for 100 seconds, and methanol gas at a concentration of 100 ppm was allowed to flow for 100 seconds so that the methanol gas is adsorbed, and then the dry air gas was allowed to flow again for 100 seconds so that the methanol gas is desorbed.

FIG. 17A shows a change rate of capacitance (arbitrary units (a.u.)) as the frequency of the voltage applied to the top electrode 220 and the bottom electrode 230 is varied to 10 kHz, 30 kHz, 100 kHz, 800 kHz, and 1 MHz under the experimental conditions described above, and FIG. 17B shows the sensitivity (response, %) according to the change of the frequency of the voltage applied to the top electrode 220 and the bottom electrode 230 under the experimental conditions described above. Here, the magnitude of the voltage applied to the top electrode 220 and the bottom electrode 230 is 1 V.

It was confirmed that in the complex gas sensor 10 according to Example 1, methanol gas could be detected in a frequency range of 800 kHz or more and 1 MHz or less as can be seen in FIG. 17. In particular, it was confirmed that the sensing sensitivity of the methanol gas was the highest when the frequency of the voltage applied to the top electrode 220 and the bottom electrode 230 is 1 MHz.

FIG. 18 is a graph illustrating toluene gas sensing characteristics according to frequency of the complex gas sensor 10 manufactured according to the embodiment of the present disclosure.

The complex gas sensor 10 manufactured according to Example 1 was stabilized by flowing dry air gas for 300 seconds, and toluene gas at a concentration of 100 ppm was allowed to flow for 300 seconds so that the toluene gas is adsorbed, and then the dry air gas was allowed to flow again for 300 seconds so that the toluene gas is desorbed.

FIG. 18A shows a change rate of capacitance (a.u.) as the frequency of the voltage applied to the top electrode 220 and the bottom electrode 230 is varied to 150 Hz, 500 Hz, 1000 Hz, 3000 Hz, and 10000 Hz under the experimental conditions described above, and FIG. 18B shows the sensitivity (response, %) according to the change of the frequency of the voltage applied to the top electrode 220 and the bottom electrode 230 under the experimental conditions described above. In addition, the magnitude of the voltage applied to the top electrode 220 and the bottom electrode 230 is 1 V.

It was confirmed that in the complex gas sensor 10 according to Example 1, the capacitance increased as the frequency of the voltage applied to the top electrode 220 and the bottom electrode 230 increases from 800 Hz to 10 kHz, but the capacitance decreased as the frequency increases from a starting point of 10 kHz as can be seen in FIG. 18. Accordingly, it can be seen that, the sensing sensitivity with respect to the toluene gas may be improved as the frequency of the voltage applied to the top electrode 220 and the bottom electrode 230 of the complex gas sensor 10 according to Example is controlled to be greater than 800 Hz and less than 10 KHz.

Preferably, in order to detect toluene gas, the detection frequency of the toluene gas is selected in the range of greater than 800 Hz and less than 10 KHz, so as not to overlap the sensing ranges of methanol and acetone, so that the gas sensor can sense multiple gases in a complex manner.

FIG. 19 is a graph illustrating acetone gas sensing characteristics according to frequency of the complex gas sensor 10 manufactured according to the embodiment of the present disclosure.

According to FIG. 19, the complex gas sensor 10 manufactured according to Example 1 was stabilized by flowing dry air gas for 300 seconds, and acetone gas at a concentration of 100 ppm was allowed to flow for 60 seconds so that the acetone gas is adsorbed, and then the dry air gas was allowed to flow again for 300 seconds so that the acetone gas is desorbed. FIG. 19A shows a change rate of capacitance (a.u.) as the frequency of the voltage applied to the top electrode 220 and the bottom electrode 230 is varied to 150 Hz, 300 Hz, 500 Hz, 800 Hz, and 1000 Hz under the experimental conditions described above, and FIG. 19B shows the sensitivity (response, %) according to the change of the frequency of the voltage applied to the top electrode 220 and the bottom electrode 230 under the experimental conditions described above. In addition, the magnitude of the voltage applied to the top electrode 220 and the bottom electrode 230 is 1 V.

It was confirmed that in the complex gas sensor 10 according to Example 1, the capacitance increased as the frequency of the voltage applied to the top electrode 220 and the bottom electrode 230 increases from 300 Hz to 1000 Hz, but the capacitance decreased as the frequency increases from a starting point of 500 Hz to 800 Hz as can be seen in FIG. 19. Accordingly, it can be seen that, the sensing sensitivity with respect to the acetone gas may be improved as the frequency of the voltage applied to the top electrode 220 and the bottom electrode 230 of the complex gas sensor 10 according to Example is controlled to be greater than 300 Hz and less than 800 Hz.

That is, in order to detect acetone gas, a frequency of greater than 300 Hz and less than 1000 Hz at which the change in capacitance occurs may be applied. Preferably, in order to detect acetone gas, the detection frequency of the acetone gas may be selected in the range of greater than 300 Hz and less than 800 Hz, so as not to overlap the sensing ranges of methanol and toluene, so that the gas sensor can sense multiple gases in a complex manner.

It can be seen that the complex gas sensor 10 according to the embodiment of the present disclosure may selectively sense any one of the methanol gas, the toluene gas, and the acetone gas according to the frequency of the voltage applied to the top electrode 220 and the bottom electrode 230 as can be seen from the above-described Experimental Example.

FIG. 20 is a graph comparing gas sensing characteristics according to frequency of the complex gas sensor 10 manufactured according to the embodiment of the present disclosure.

Referring to FIG. 20, a change in capacitance over time was measured and shown after flowing methanol gas, toluene gas, and acetone gas into the complex gas sensor 10 manufactured according to Example 1. More specifically, the methanol gas was measured under the condition that the frequency of the voltage applied to the top electrode 220 and the bottom electrode 230 was 1 MHz, the toluene gas was measured under the condition that the frequency was 1000 Hz, and the acetone gas was measured under the condition that the frequency was 500 Hz. In addition, the time (sec) shown in FIG. 20 refers to the time during which the gas flows, and this means that as time increases, the concentration of the gas also increases.

It was confirmed that, in the complex gas sensor 10 according to Example 1, the capacitance was changed according to the adsorption of the methanol gas, the toluene gas, and the acetone gas, and sensing sensitivity was increased as the gas concentration increases as can be seen in FIG. 20.

In order to confirm the sensing characteristics for volatile organic compounds in addition to the above-described sensing of the methanol gas, the toluene gas, and the acetone gas, the volatile organic compounds were flowed to the complex gas sensor 10 according to Example at concentrations of 5 ppm, 10 ppm, 20 ppm, 50 ppm, and 100 ppm, and a change in capacitance was measured by analyzing with an LCR meter. It can be seen that, in the complex gas sensor 10 according to Example, the change in capacitance occurs even for the volatile organic compounds, and accordingly, the volatile organic compounds can be easily sensed. More specific experimental conditions are summarized in Table 2 below.

TABLE 2

| VOCs MFC (500 ppm) | Air MFC (99.99%) | Concentration (ppm) |
|---|---|---|
| 5 | 495 | 5 |
| 10 | 490 | 10 |
| 20 | 480 | 20 |
| 50 | 450 | 50 |
| 100 | 400 | 100 |

FIG. 21 is a graph illustrating sensitivity according to a concentration of gas provided to the complex gas sensor 10 according to the embodiment of the present disclosure, FIG. 22 is a graph illustrating a response time according to the concentration of gas provided to the complex gas sensor 10 according to the embodiment of the present disclosure, and FIG. 23 is a graph illustrating a recovery time according to the concentration of gas provided to the complex gas sensor 10 according to the embodiment of the present disclosure.

Referring to FIGS. 21 to 23, methanol gas, toluene gas, and acetone gas were flowed into the complex gas sensor 10 according to Example 1, and the sensitivity (response, %), response time (T90, sec), and recovery time (D10, sec) according to each gas concentration were measured and shown. The measurement results of FIGS. 21 to 23 are summarized in Tables 3 to 5 below.

TABLE 3

| | Methanol | | | | |
|---|---|---|---|---|---|
| | 5 ppm | 10 ppm | 20 ppm | 50 ppm | 100 ppm |
| Response (%) | 0.020 | 0.025 | 0.043 | 0.074 | 0.098 |
| Response Time (sec) | 61.4 | 43.0 | 30.0 | 22.8 | 23.4 |
| Recovery Time (sec) | 45.6 | 34.2 | 36.4 | 33.8 | 32.8 |

TABLE 4

| | Toluene | | | | |
|---|---|---|---|---|---|
| | 5 ppm | 10 ppm | 20 ppm | 50 ppm | 100 ppm |
| Response (%) | 0.010 | 0.017 | 0.028 | 0.072 | 0.088 |
| Response Time (sec) | 65.6 | 49.8 | 39.2 | 35.4 | 24.8 |
| Recovery Time (sec) | 62.6 | 50.8 | 51.4 | 52.2 | 49.4 |

TABLE 5

| | Acetone | | | | |
|---|---|---|---|---|---|
| | 5 ppm | 10 ppm | 20 ppm | 50 ppm | 100 ppm |
| Response (%) | — | 0.038 | 0.054 | 0.118 | 0.117 |
| Response Time (sec) | — | 80.6 | 52 | 61.5 | 52.2 |
| Recovery Time (sec) | — | 85.6 | 65.2 | 69.2 | 93.8 |

It was confirmed that the complex gas sensor 10 according to Example 1 showed a high R-square value of 0.87 or more for all of the methanol gas, the toluene gas, and the acetone gas as can be seen in FIGS. 21 to 23 and Tables 3 to 5. In addition, it was confirmed that the complex gas sensor 10 according to Example 1 showed a fast response time and recovery time of less than 100 seconds for all of the methanol gas, the toluene gas, and the acetone gas.

Since a kinetic diameter of the methanol gas is 3.80 Å, a kinetic diameter of the toluene gas is 5.80 Å, and a kinetic diameter of the acetone gas is 4.70 Å, the methanol gas is adsorbed and desorbed faster than other gases. In addition, since toluene has π-π bonding in a carbon lattice due to a $sp^2$ bond of graphene and thus adsorption and desorption of a weak bond are achieved by the π-π bonding, a difference occurs in adsorption and desorption characteristics compared to the methanol gas.

Experimental Example 4: Sensitivity Characteristics of Complex Gas Sensor 10 According to One Embodiment As described above, the complex gas sensor 10 according to one embodiment of the present disclosure uses photo-active energy to improve detection characteristics of the target gas. Hereinafter, sensitivity characteristics of the complex gas sensor 10 using photo-active energy will be described in detail with reference to the drawings.

Experiments for sensitivity characteristics were performed at room temperature, and a change in capacitance was measured by applying a voltage of a fixed frequency to the gas detection part 200 manufactured according to Example 1.

The change in capacitance of the gas detection part 200 was measured by alternately injecting dry air and the target gas at predetermined time intervals. In addition, in order to check measurement linearity according to concentration, the change in capacitance was measured by analyzing with an LCR meter while gradually increasing the concentration of the target gas injected into the complex gas sensor 10 to 100, 200, 300, 500, and 800 ppb as shown in Table 6.

TABLE 6

| TARGET GAS (10 ppm) | Air MFC (99.99%) | Concentration(ppb) |
|---|---|---|
| 5 | 495 | 100 |
| 10 | 490 | 200 |
| 15 | 485 | 300 |
| 25 | 475 | 500 |
| 40 | 460 | 800 |

Since the measurable target gas is selected according to the frequency of the voltage applied to the complex gas sensor 10 as described above, the sensitivity characteristics were measured while changing the frequency of the voltage applied to the electrode for each target gas.

In addition, in order to measure the sensor sensitivity according to the photo-active energy, a change in capacitance was measured while irradiating light from the light source 100, and the change in capacitance was measured without irradiating the light from the light source 100 under the same measurement conditions.

FIG. 24 is a graph showing methanol gas detection characteristics of the complex gas sensor 10 according to one embodiment of the present disclosure.

The change in capacitance was measured while fixing the voltage applied to the gas detection part 200 to 1 MHz, which is a detection frequency of methanol gas, and injecting the methanol gas according to the above-described experimental conditions.

It can be seen that, when the light is irradiated from the light source 100 (when photo-active energy is used), the change in capacitance is greater than when the light is not irradiated from the light source 100 as can be seen in FIG. 24A that shows the change in capacitance over time.

When the light source 100 is turned on and light is irradiated to the sensitive part 240, active energy of a sensitive material is increased by the light energy, so that the target gas is more actively adsorbed. As described above, when the adsorption of the target gas is active, a change in permittivity is active and thus the change in capacitance is increased.

It can be confirmed that, in the case of using the photo-active energy, the sensitivity is increased by a factor of 11 or more as compared to the case in which the photo-active energy is not used as can be seen in FIG. 24A and Table 7.

US 12,601,678 B2

23

TABLE 7

| Methanol Concentration (ppb) | Response without UV Light ($\Delta C/C_0$, %) | Response with UV Light ($\Delta C/C_0$, %) |
|---|---|---|
| 100 | 0.001 | 0.2048 |
| 200 | 0.002 | 0.2204 |
| 300 | 0.009 | 0.2373 |
| 500 | 0.013 | 0.2405 |
| 800 | 0.022 | 0.2446 |

In addition, it was confirmed that the linearity of the change in capacitance was increased when the methanol is injected at each of gas concentrations of 100, 200, 300, 500, and 800 ppb. It was confirmed that linearity ($R^2$=0.8902) with light irradiation was greater than linearity ($R^2$=0.8753) without light irradiation.

The methanol gas has $\pi$-$\pi$ bonding in the carbon lattice due to a sp2 bond with functional groups such as a hydroxyl group and a carboxyl group of graphene, which is a sensitive material. The above-described measurement is performed by measuring the change in capacitance caused by the adsorption and desorption of the methanol having the $\pi$-$\pi$ bond.

In addition, it was confirmed that, by supplying the photo-active energy to the sensitive material through light irradiation, the adsorption of the methanol gas was improved, the sensitivity of the complex gas sensor 10 for the methanol gas was improved, and the measurement stability (=linearity) was increased.

FIG. 25 is a graph showing toluene gas detection characteristics of the complex gas sensor 10 using photo-active energy according to one embodiment of the present disclosure.

The change in capacitance was measured while fixing the voltage applied to the gas detection part 200 to 1,000 Hz, which is a detection frequency of toluene gas, and injecting the toluene gas according to the above-described experimental conditions.

It can be seen that, when the light is irradiated from the light source 100 (when photo-active energy is used), the change in capacitance is greater than when the light is not irradiated from the light source 100 as can be seen in FIG. 25A that shows the change in capacitance over time.

When the light source 100 is turned on and light is irradiated to the sensitive part 240, active energy of a sensitive material is increased by the light energy, so that the target gas is more actively adsorbed. As described above, when the adsorption of the target gas is active, a change in permittivity is active and thus the change in capacitance is increased.

It can be confirmed that, in the case of using the photo-active energy, the sensitivity is increased by a factor of 17 or more at 800 ppb as compared to the case in which the photo-active energy is not used as can be seen in FIG. 25A and Table 8.

TABLE 8

| Toluene Concentration (ppb) | Response without UV Light ($\Delta C/C_0$, %) | Response with UV Light ($\Delta C/C_0$, %) |
|---|---|---|
| 100 | 0.001 | 0.2405 |
| 200 | 0.002 | 0.2539 |
| 300 | 0.009 | 0.2576 |
| 500 | 0.013 | 0.2710 |
| 800 | 0.022 | 0.3859 |

In addition, it was confirmed that, as shown in FIG. 25B, the change in capacitance had high linearity ($R^2$=0.8753), when toluene was injected at each of gas concentrations of 100, 200, 300, 500, and 800 ppb.

The toluene gas has $\pi$-$\pi$ bonding in the carbon lattice due to a sp2 bond with functional groups such as a hydroxyl group and a carboxyl group of graphene, which is a sensitive material. The above-described measurement is performed by measuring the change in capacitance caused by the adsorption and desorption of the toluene having the $\pi$-$\pi$ bond.

In addition, it was confirmed that, by supplying photo-active energy to the sensitive material through light irradiation, the adsorption of the toluene gas was improved, the sensitivity of the complex gas sensor 10 for the toluene gas was improved, and the measurement stability (=linearity) was increased.

FIG. 26 is a graph showing acetone gas detection characteristics of the complex gas sensor 10 using photo-active energy according to one embodiment of the present disclosure.

The change in capacitance was measured while fixing the voltage applied to the gas detection part 200 to 500 Hz, which is a detection frequency of acetone gas, and injecting the acetone gas according to the above-described experimental conditions.

It can be seen that, when light is irradiated from the light source 100, the change in capacitance of the complex gas sensor 10 is greater than when the light is not irradiated from the light source 100 as can be seen in FIG. 26A that shows the change in capacitance over time.

When the light source 100 is turned on and light is irradiated to the sensitive part 240, active energy of a sensitive material is increased by the light energy, so that the target gas is more actively adsorbed. As described above, when the adsorption of the target gas is active, a change in permittivity is active and thus the change in capacitance is increased.

TABLE 9

| Acetone Concentration (ppb) | Response without UV Light ($\Delta C/C_0$, %) | Response with UV Light ($\Delta C/C_0$, %) |
|---|---|---|
| 100 | 0.001 | 0.1721 |
| 200 | 0.002 | 0.2472 |
| 300 | 0.009 | 0.2666 |
| 500 | 0.013 | 0.2787 |
| 800 | 0.022 | 0.3771 |

It can be confirmed that, in the case of using the photo-active energy, the sensitivity is increased by a factor of 17 or more at 800 ppb as compared to the case in which the photo-active energy is not used as can be seen in FIG. 26A and Table 9.

In addition, it was confirmed that, as shown in FIG. 26B, the change in capacitance had high linearity (R2=0.8753), when acetone was injected at each of gas concentrations of 100, 200, 300, 500, and 800 ppb.

The above-described measurement is performed by measuring the change in capacitance caused by the adsorption and desorption of acetone gas, which has a large dipole moment, with functional groups such as a hydroxyl group and a carboxyl group of graphene, which is a sensitive material.

In addition, it was confirmed that, by supplying the photo-active energy to the sensitive material through light irradiation, the adsorption of the acetone gas was improved, the sensitivity of the complex gas sensor 10 for the acetone gas was improved, and the measurement stability (=linearity) was increased.

Experimental Example 6: Characteristics of
Sensitive Composite

Hereinafter, characteristics of a sensitive composite 280 included in a complex gas sensor 20 according to another embodiment will be described in detail with reference to the drawings. At this time, the sensitive composite 280 includes graphene as a sensitive part 240, and a ZnO quantum dot as a photo-active part 250.

FIG. 27 is a result of XRD analysis of the sensitive part 240 according to one embodiment.

Referring to FIG. 27, it was confirmed that, in the case of graphene, a hexagonal phase of carbon (JCPDS number: 26-1080) was formed. In addition, it was confirmed that, in the case of the sensitive composite 280 including graphene and a ZnO quantum dot, phases of hexagonal structure of carbon of graphene and the ZnO quantum dot were mixed. In addition, other peaks other than carbon and ZnO phases are not observed in the sensitive composite 280 including the graphene and the ZnO quantum dot. Accordingly, it was confirmed that high purity graphene and ZnO quantum dot without impurities formed a complex phase in the sensitive composite 280.

Meanwhile, the sensitive composite 280 includes a sensitive part 240 formed by stacking a sensitive material in a nanometer scale and a quantum dot having optical characteristics.

FIG. 28 is an image of the sensitive composite 280 included in the complex gas sensor 20 according to another embodiment of the present disclosure.

FIG. 28 is a TEM image of the sensitive composite 280 including graphene as a sensitive material and a ZnO quantum dot, and it can be confirmed that the sensitive composite 280 includes the sensitive part 240 formed by stacking graphene as multi-layer graphene and a photo-active part 250 formed of a ZnO quantum dot coated on an upper end of the sensitive part 240. Here, it can be confirmed that the photo-active part 250 is formed by including a circular-shaped ZnO quantum dot and has a size of about 8 nm.

FIG. 29 is a result of analyzing the sensitive composite 280 according to one embodiment according to an X-ray photoelectron spectroscopy (XPS) method. The sensitive composite 280 may include a carboxyl group (—COOH) and a hydroxyl group (—OH) as functional groups to adsorb and desorb a target gas.

Referring to FIG. 29, the sensitive composite 280 includes a peak of 288.8 eV corresponding to C—O—O, a peak of 287.8 eV corresponding to C=O, and a peak of 286.3 eV corresponding to C—OH, and a peak of 284.8 eV corresponding to $sp^3$ bonded carbon, and a peak of 284 eV corresponding to $sp^2$ bonded carbon are shown. In addition, a peak of 533.1 eV corresponding to O—H and peaks of 534.8 eV and 531.9 eV respectively corresponding to O—C and C—O—O—H are shown. It can be confirmed from the existence of these peaks that a carboxyl group (—COOH) and a hydroxyl group (—OH) are abundantly present in the sensitive composite according to one embodiment.

The sensitive material and the active material included in the sensitive composite 280 absorb the light irradiated from the light source 100. Light transmittance of the sensitive material has been described in FIG. 16. FIG. 30 is a graph showing optical characteristics of the ZnO quantum dot, which is an active material.

FIG. 30A is a spectrum result of a UV visible spectrophotometer (UV-vis) of the ZnO quantum dot. As shown in FIG. 30A, when a reaction was performed for 10 minutes, an absorption peak was not observed, and thus it was confirmed that the ZnO quantum dot was not formed. However, it was confirmed that the absorption peak was shown at 358 nm at the time of 30 minutes, and a red-shift occurred as time increased, and thus, the quantum dot was gradually increased in size.

FIG. 30B is a result of a photoluminescence (PL) analysis of the ZnO quantum dot. Referring to FIG. 30B, at 10 minutes, there was no light emission characteristic, but it was confirmed that light was emitted from 30 minutes, and a light emission peak was the highest at 4 hours. Accordingly, the optimal manufacturing conditions for the ZnO quantum dot, which exhibited the best light characteristic when the ZnO quantum dot was prepared for 4 hours, were confirmed.

Experimental Example 7: Sensitivity Characteristics
of Complex Gas Sensor 20 According to Another
Embodiment As described above, the complex gas sensor 20 according to another embodiment of the present disclosure includes the sensitive composite 280, and detects the target gas through the change in capacitance, which changes as the sensitive composite 280 adsorbs the target gas. Hereinafter, sensitivity characteristics of the complex gas sensor 20 according to another embodiment according to the supply of photo-active energy will be described in detail with reference to the drawings.

Experiments for sensitivity characteristics were performed at room temperature, and a change in capacitance was measured by applying a voltage of a fixed frequency to a gas detection part 201 having an electrode formed in a shape according to Example 1.

For the experiment, the change in capacitance of the gas detection part 201 was measured by alternately injecting dry air and the target gas at predetermined time intervals. In addition, in order to check measurement linearity according to concentration, the change in capacitance was measured by analyzing with an LCR meter while gradually increasing the concentration of methanol gas injected into the complex gas sensor 20 to 100, 200, 300, 500, and 800 ppb as shown in Table 10.

TABLE 10

| TARGET GAS (10 ppm) | Air MFC (99.99%) | Concentration(ppb) |
|---|---|---|
| 5 | 495 | 100 |
| 10 | 490 | 200 |
| 15 | 485 | 300 |
| 25 | 475 | 500 |
| 40 | 460 | 800 |

Meanwhile, since the measurable target gas is selected according to the frequency of the voltage applied to the complex gas sensor 20 as described above, the sensitivity characteristics were measured while changing the frequency of the voltage applied to the electrode for each target gas.

In addition, in order to measure the sensor sensitivity according to the photo-active energy, a change in capacitance was measured while irradiating light from the light source 100, and the change in capacitance was measured without irradiating light from the light source 100 under the same measurement conditions.

FIG. 31 is a graph showing methanol gas detection characteristics of the complex gas sensor 20 according to another embodiment of the present disclosure.

The change in capacitance was measured while fixing the voltage applied to the gas detection part 201 to 1 MHz, which is a detection frequency of methanol gas, and injecting the methanol gas according to the above-described experimental conditions.

It can be seen that, when the light is irradiated from the light source 100 (when photo-active energy is used), the change in capacitance is greater than when the light is not irradiated from the light source 100 as can be seen in FIG. 31A that shows the change in capacitance over time.

When the light source 100 is turned on and light is irradiated to the sensitive part 240, active energy of a sensitive material is increased by the light energy, so that the target gas is more actively adsorbed. As described above, when the adsorption of the target gas is active, a change in permittivity is active and thus the change in capacitance is increased.

TABLE 11

| Methanol Concentration (ppb) | Response of EGs without UV Light ($\Delta C/C_0$, %) | Response of EGs-ZnO QDs with UV Light ($\Delta C/C_0$, %) |
|---|---|---|
| 100 | 0.001 | 0.2228 |
| 200 | 0.002 | 0.2628 |
| 300 | 0.009 | 0.3681 |
| 500 | 0.013 | 0.4098 |
| 800 | 0.022 | 0.4554 |

It can be confirmed that, in the case of using the photo-active energy, the sensitivity is increased by a factor of 20 or more as compared to the case in which the photo-active energy is not used as can be seen in FIG. 31A and Table 11.

In addition, it was confirmed that the linearity of the change in capacitance was increased when methanol is injected at each of gas concentrations of 100, 200, 300, 500, and 800 ppb as shown in FIG. 31B. It was confirmed that linearity ($R^2$=0.9374) with light irradiation was greater than linearity ($R^2$=0.8753) without light irradiation.

The methanol gas has $\pi$-$\pi$ bonding in the carbon lattice due to a sp2 bond with functional groups such as a hydroxyl group and a carboxyl group of graphene, which is a sensitive material. The above-described measurement is performed by measuring the change in capacitance caused by the adsorption and desorption of the methanol having the $\pi$-$\pi$ bond.

In addition, it was confirmed that, by supplying the photo-active energy to the sensitive composite 280 through light irradiation, the adsorption of the methanol gas was improved, the sensitivity of the complex gas sensor 20 for the methanol gas was improved, and the measurement stability (=linearity) was increased.

FIG. 32 is a graph showing toluene gas detection characteristics of the complex gas sensor 20 according to another embodiment of the present disclosure.

The change in capacitance was measured while fixing the voltage applied to the gas detection part 201 at 1,000 Hz, which is a detection frequency of toluene gas, and injecting the toluene gas according to the above-described experimental conditions.

It can be seen that, when the light is irradiated from the light source 100 (when photo-active energy is used), the change in capacitance is greater than when the light is not irradiated from the light source 100 as can be seen in FIG. 32A that shows the change in capacitance over time.

When the light source 100 is turned on and light is irradiated to the sensitive part 240, active energy of a sensitive material is increased by the light energy, so that the target gas is more actively adsorbed. As described above, when the adsorption of the target gas is active, a change in permittivity is active and thus the change in capacitance is increased.

TABLE 12

| Toluene Concentration (ppb) | Response of EGs without UV Light ($\Delta C/C_0$, %) | Response of EGs-ZnO QDs with UV Light ($\Delta C/C_0$, %) |
|---|---|---|
| 100 | 0.001 | 0.4558 |
| 200 | 0.002 | 0.4804 |
| 300 | 0.009 | 0.5241 |
| 500 | 0.013 | 0.6037 |
| 800 | 0.022 | 0.6802 |

It can be confirmed that, in the case of using the photo-active energy, the sensitivity is increased by a factor of 31 or more as compared to the case in which the photo-active energy is not used as can be seen in FIG. 32A and Table 12.

In addition, it was confirmed that, as shown in FIG. 32B, linearity ($R^2$=0.9031) was high in which the change in capacitance is increased, when toluene was injected at each of gas concentrations of 100, 200, 300, 500, and 800 ppb.

The toluene gas has $\pi$-$\pi$ bonding in the carbon lattice due to a sp2 bond with functional groups such as a hydroxyl group and a carboxyl group of graphene, which is a sensitive material. The above-described measurement is performed by measuring the change in capacitance caused by the adsorption and desorption of the toluene having the $\pi$-$\pi$ bond.

In addition, it was confirmed that, by supplying photo-active energy to the sensitive material through light irradiation, the adsorption of the toluene gas was improved, the sensitivity of the complex gas sensor 20 for the toluene gas was improved, and the measurement stability (=linearity) was increased.

FIG. 33 is a graph showing acetone gas detection characteristics of the complex gas sensor 20 according to another embodiment of the present disclosure.

The change in capacitance was measured while fixing the voltage applied to the gas detection part 201 to 500 Hz, which is a detection frequency of acetone gas, and injecting the acetone gas according to the above-described experimental conditions.

It can be seen that, when light is irradiated from the light source 100, the change in capacitance of the complex gas sensor 20 is greater than when the light is not irradiated from the light source 100 as can be seen in FIG. 33A that shows the change in capacitance over time.

When the light source 100 is turned on and light is irradiated to the sensitive part 240, active energy of a sensitive material is increased by the light energy, so that the target gas is more actively adsorbed. As described above, when the adsorption of the target gas is active, a change in permittivity is active and thus the change in capacitance is increased.

TABLE 13

| Acetone Concentration (ppb) | Response of EGs without UV Light ($\Delta C/C_0$, %) | Response of EGs-ZnO QDs with UV Light ($\Delta C/C_0$, %) |
|---|---|---|
| 100 | 0.001 | 0.4770 |
| 200 | 0.002 | 0.4705 |
| 300 | 0.009 | 0.5319 |

TABLE 13-continued

| Acetone Concentration (ppb) | Response of EGs without UV Light ($\Delta C/C_0$, %) | Response of EGs-ZnO QDs with UV Light ($\Delta C/C_0$, %) |
| --- | --- | --- |
| 500 | 0.013 | 0.5935 |
| 800 | 0.022 | 0.6701 |

It can be confirmed that, in the case of using the photo-active energy, the sensitivity is increased by a factor of 31 or more at 800 ppb as compared to the case in which the photo-active energy is not used as can be seen in FIG. 33A and Table 13.

In addition, it was confirmed that, as shown in FIG. 33B, linearity ($R^2$=0.8243) was high in which the change in capacitance is increased, when acetone was injected at each of gas concentrations of 100, 200, 300, 500, and 800 ppb.

The above-described measurement is performed by measuring the change in capacitance caused by the adsorption and desorption of acetone gas, which has a large dipole moment, with functional groups such as a hydroxyl group and a carboxyl group of graphene, which is a sensitive material.

In addition, it was confirmed that, by supplying the photo-active energy to the sensitive material through light irradiation, the adsorption of the acetone gas was improved, the sensitivity of the complex gas sensor 20 for the acetone gas was improved, and the measurement stability (=linearity) was increased. Although the present disclosure has been described in detail with reference to the exemplary embodiments, the scope of the present disclosure is not limited to a specific embodiment, and should be interpreted by the appended claims. In addition, it will be understood that many modifications and variations can be made by those skilled in the art without departing from the scope of the present disclosure.

Industrial Availability

The present is about a gas detection device using a thermochemical discoloration sensor and its manufacturing method. It can be used in various forms because it can easily check the presence of hydrogen gas by color conversion. When it is in non-contact with hydrogen gas, it includes reversible properties that recover to its original color or irreversible properties that maintain a changed color, and thus can be used in various forms. In addition, the discoloration sensor of this invention can be used in the form of tape and spray, so there is a high industrial possibility that it can be used in images, subzero temperatures, and various attachment places.

What is claimed is:

1. A complex gas sensor comprising:
a light source configured to irradiate light; and
a gas detection part in which adsorption of a target gas is promoted by the light and whose capacitance changes according to the adsorption of the target gas,
wherein the gas detection part comprises a photo-active part comprising quantum dot that absorbs energy of the light and promotes polarization in a sensing part.

2. The complex gas sensor of claim 1, wherein the gas detection part includes:
a top electrode surrounding the sensitive part;
a bottom electrode facing the top electrode; and
a porous structure disposed between the top electrode and the bottom electrode.

3. The complex gas sensor of claim 2, wherein in the gas detection part, a frequency of a voltage applied to the top electrode and the bottom electrode is differently controlled according to a type of the target gas.

4. The complex gas sensor of claim 3, wherein the target gas includes any one of methanol gas, toluene gas, and acetone gas, and
any one of the methanol gas, the toluene gas, and the acetone gas is selectively sensed according to the frequency of the voltage applied to the top electrode and the bottom electrode.

5. The complex gas sensor of claim 3, further comprising a control part configured to control a frequency of a voltage applied to the gas detection part to be greater than 800 Hz and less than 3,000 Hz, and sense toluene gas based on a change in capacitance of the gas detection part.

6. The complex gas sensor of claim 3, further comprising a control part configured to control a frequency of a voltage applied to the gas detection part to be 300 Hz or more and 800 Hz or less, and sense acetone gas based on a change in capacitance of the gas detection part.

7. The complex gas sensor of claim 3, further comprising a control part configured to control a frequency of a voltage applied to the gas detection part to be 10 KHz or more and 1 MHz or less, and sense methanol gas based on a change in capacitance of the gas detection part.

8. The complex gas sensor of claim 2, wherein the porous structure includes any one of anodic aluminum oxide (AAO), silicon oxide ($SiO_2$), polyimide (PI), polyethylene terephthalate (PET), polyethylene naphthalate (PEN), and polytetrafluoroethylene (PTFE).

9. The complex gas sensor of claim 1, wherein in the sensing part, a polarization phenomenon occurs by light energy irradiated from the light source, and the adsorption of the target gas is promoted by the polarization phenomenon.

10. The complex gas sensor of claim 1, wherein the functional groups further comprises a carboxyl group (—COOH).

11. The complex gas sensor of claim 1, wherein the sensing part further comprises any one of carbon nanotube (CNT), amorphous carbon, active carbon, and biochar as the sensitive material.

12. The complex gas sensor of claim 1, wherein the light source emits light in a wavelength of an ultraviolet region, and
in the sensing part, a polarization phenomenon occurs by absorbing the light in the wavelength of an ultraviolet region, and the adsorption of the target gas is promoted according to the polarization phenomenon.

13. A method of controlling the complex gas sensor of claim 1, the method comprising:
irradiating light to the gas detection part by controlling the light source;
applying a voltage having a detection frequency to the gas detection part;
detecting the change in capacitance of the gas detection part; and
sensing the target gas based on a change in capacitance.

14. The method of claim 13, wherein the applying of the voltage having the detection frequency to the gas detection part further includes determining the detection frequency according to a type of the target gas to be detected.

15. The method of claim 13, wherein the sensing of the target gas further includes sensing the target gas when the change in capacitance exceeds a preset reference.

16. A method of manufacturing a complex gas sensor, the method comprising:

preparing a porous structure;

forming a top electrode on an upper surface of the porous structure such that one region of the upper surface of the porous structure is exposed;

forming a bottom electrode on a lower surface of the porous structure;

forming a sensitive part configure to adsorb and desorb a target gas in the exposed region of the upper surface of the porous structure; and providing a light source configured to irradiate light to at least a portion of the sensitive part, wherein the forming of the sensitive part includes:

preparing a sensitive material in which the adsorption of the target gas is promoted by light energy irradiated from the light source;

preparing a source solution by mixing a solvent with the sensitive material; and providing the source solution to the exposed region of the upper surface of the porous structure while the porous structure is heat-treated.

17. A complex gas sensor comprising:

a light source configured to irradiate light; and a gas detection part of which capacitance changes according to adsorption of a target gas, wherein the gas detection part includes:

a sensitive composite including a sensing part configured to adsorb the target gas and a photo-active part configured to promote the adsorption of the target gas of the sensing part by light energy supplied from the light source;

a top electrode surrounding the sensitive composite;

a bottom electrode facing the top electrode; and a porous structure disposed between the top electrode and the bottom electrode, wherein the photo-active part comprises quantum dot that absorbs the light energy and promotes polarization in the sensing part.

18. A method of manufacturing the complex gas sensor of claim 17, the method comprising:

preparing a porous structure;

forming a top electrode on an upper surface of the porous structure such that one region of the upper surface of the porous structure is exposed;

forming a bottom electrode on a lower surface of the porous structure;

forming, in the exposed region of the upper surface of the porous structure, a sensitive composite including a sensing part configured to adsorb and desorb a target gas and a photo-active part configured to promote the adsorption of the target gas; and providing a light source configured to irradiate light to at least a portion of the sensitive composite.

19. A method of controlling the complex gas sensor of claim 17, the method comprising:

irradiating light to the gas detection part by controlling the light source;

applying a voltage having a detection frequency to the gas detection part;

detecting a change in capacitance of the gas detection part; and sensing the target gas based on a change in capacitance.

* * * * *